US006951757B2

(12) United States Patent
Sabatini

(10) Patent No.: US 6,951,757 B2
(45) Date of Patent: *Oct. 4, 2005

(54) TRANSFECTION METHOD AND USES RELATED THERETO

(75) Inventor: David M. Sabatini, Cambridge, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/379,130

(22) Filed: Mar. 4, 2003

(65) Prior Publication Data

US 2003/0228694 A1 Dec. 11, 2003

Related U.S. Application Data

(63) Continuation of application No. 09/817,003, filed on Mar. 22, 2001, which is a continuation-in-part of application No. 09/664,297, filed on Sep. 18, 2000, now Pat. No. 6,544,790.
(60) Provisional application No. 60/193,580, filed on Mar. 30, 2000, and provisional application No. 60/154,737, filed on Sep. 17, 1999.

(51) Int. Cl.$^7$ ........................ C12N 15/63; C12N 15/85; C12N 15/00
(52) U.S. Cl. ..................... 435/455; 435/320.1; 435/174
(58) Field of Search ............................ 435/455, 320.1, 435/174, 458

(56) References Cited

U.S. PATENT DOCUMENTS

| | | |
|---|---|---|
| 4,591,567 A | 5/1986 | Britten et al. |
| 5,445,934 A | 8/1995 | Fodor et al. |
| 5,654,185 A | 8/1997 | Palsson |
| 5,744,305 A | 4/1998 | Fodor et al. |
| 5,750,346 A | 5/1998 | Bridgham et al. |
| 5,804,431 A | 9/1998 | Palsson |
| 5,807,522 A | 9/1998 | Brown et al. |
| 5,811,274 A | 9/1998 | Palsson |
| 5,851,818 A | 12/1998 | Huang et al. |
| 6,025,337 A | 2/2000 | Truong et al. |
| 6,110,426 A | 8/2000 | Shalon et al. |
| 6,133,026 A | 10/2000 | Huang et al. |
| 6,544,790 B1 * | 4/2003 | Sabatini ...................... 435/455 |

FOREIGN PATENT DOCUMENTS

| | | |
|---|---|---|
| WO | WO 95 35505 | 12/1995 |
| WO | WO 96 17948 | 6/1996 |
| WO | WO 99 55886 | 11/1999 |
| WO | WO 99 57311 | 11/1999 |
| WO | WO 99 57312 | 11/1999 |
| WO | WO 00 63407 | 10/2000 |

OTHER PUBLICATIONS

Anchordoquy, T. J. et al., "Maitenance of transfection rates and physical characterization of lipid/DNA complexes after freeze–drying and rehydration," Arch. Biochem. Biophys. 348:199–206 (1997).
Anchordoquy, T. J. et al., "Stability of lipid/DNA complexes during agitation and freeze–thawing," J. Pharm. Sci. 87:1046–51 (1998).
Bielinska, A. U. et al., "DNA complexing with polyamidoamine dendrimers: implications for transfection," Bioconjug. Chem. 10:843–50 (1999).
Cherng, J. Y. et al., "Freeze–drying of poly((2–dimethylamino)ethyl methacrylate)–based gene delivery systems," Pharm. Res. 14:1838–41 (1997).
Eastman, S. J. et al., "Biophysical characterization of cationic lipid: DNA complexes," Biochim. Biophys. Acta 1325:41–62 (1997).
Hong, K. et al., "Stabilization of cationic liposome–plasmid DNA complexes by polyamines and poly(ethylene glycol)–phospholipid conjugates for efficient in vivo gene delivery," FEBS Lett. 400:233–37 (1997).
Kalyanasundaram, Subramanian, et al., "Coacervate Microspheres as Carriers of Recombinant Adenoviruses," Cancer Gene Therapy, 6:107–112 (1999).
Leong, K. W. et al., "DNA–polycation nanospheres as non–viral gene delivery vehicles," Journal of Controlled Release 53:183–193 (1998).
Lueking, A. et al., "Protein microarrays for gene expression and antibody screening," Anal. Biochem. 270:103–11 (1999).
MacBeath, G., et al., "Printing proteins as microarrays for high–throughput function determination," Science 289:1760–63 (2000).
Pires, P. et al., "Interaction of cationic liposomes and their DNA complexes with monocytic leukemia cells," Biochim. Biophys. Acta 1418:71–84 (1999).
Russell, D. W., et al., "Human gene targeting by viral vectors," Nat. Genet. 18:325–30 (1998).
Schena, M., "Genome analysis with gene expression microarrays," BioEssays 18:427–431 (1996).
Schena, M., et al., "Parallel human genome alaysis: Microarray–based expression monitoring of 1000 genes," Proc. Natl. Sci. USA 93:10614–10619 (1995).

(Continued)

Primary Examiner—Terry McKelvey
Assistant Examiner—Nancy T. Vogel
(74) Attorney, Agent, or Firm—Clark & Elbing LLP; Kristina Bieker-Brady

(57) ABSTRACT

The invention features a method of introducing nucleic acid molecules into eukaryotic cells by (a) depositing a nucleic acid molecule-containing mixture onto a surface, (b) affixing the nucleic acid molecule-containing mixture to the surface, and (c) plating eukaryotic cells onto the surface under appropriate conditions for entry of the nucleic acid molecules into the cells.

36 Claims, 7 Drawing Sheets

OTHER PUBLICATIONS

Schena, M., et al., "Microarrays: Biotechnology's discovery platform for functional genomics," *Tibtech,* 16:301–306 (1998).

Simonsen, H., et al., "Cloning by function: Expression cloning in mammalian cells," *TiPS* 15:437–441 (1994).

Stegmann, T., et al., "Gene transfer mediated by cationic lipids: Lack of correlation between lipid mixing and transfection," *Biochim. Biophys. Acta* 1325:71–9 (1997).

Strausberg, R. L., et al., "The mammalian gene collection," *Science* 286:455–457 (1999).

Talsma, H., et al., "Stabilization of gene delivery systems by freeze–drying," *Int. J. Pharm.* 157:233–238 (1997).

Truong–Le, Vu L., et al., "Gene Transfer by DNA–Gelatin Nanospheres," *Archives of Biochemistry and Biophysics,* 361:47–56 (1999).

Truong–Le, Vu L., et al., "Controlled Gene Delivery by DNA–Gelatin Nanospheres," *Human Gene Therapy,* 9:1709–1717 (1998).

Uyttersprot, N., et al., "A new tool for efficient transfection of dog and human thyrocytes in pimary culture," *Mol. Cell. Endocrinol.* 142:35–39 (1998).

Whitney, M.A., et al., "A genome–wide functional assay of signal transduction in living mammalian cells," *Nat. Biotechnol.* 16:1329–33 (1998).

Zanta, M., et al., "Gene delivery: A single nuclear localization signal peptide is sufficient to carry DNA to the cell nucleus," *Proc. Natl. Acad. Sci. U.S.A.* 96:91–96 (1999).

Zhu, H., et al., "Analysis of yeast protein kinases using protein chips," *Nat. Genet.* 26:283–289 (2000).

Ziauddin, J., et al., "Microarrays of cells expressing defined cDNAs," *Nature* 411:107–110 (2001).

* cited by examiner

HEK293T cells reverse transfected with HA-GST and detected via anti-HA immunofluorescence

TRANSFECTION METHOD AND USES RELATED THERETO

CROSS-REFERENCE TO RELATED APPLICATIONS

This is a continuation of U.S. patent application Ser. No. 09/817,003, filed Mar. 22, 2001 (now pending), which is a continuation-in-part of U.S. patent application Ser. No. 09/664,297, filed Sep. 18, 2000 (now U.S. Pat. No. 6,544,790), which in turn claims the benefit of U.S. Provisional Application No. 60/193,580, filed Mar. 30, 2000, and U.S. Provisional Application No. 60/154,737, filed Sep. 17, 1999 (each of which is now abandoned). The entire teachings of each of the above-referenced applications are incorporated herein by reference.

BACKGROUND OF THE INVENTION

Genome and expressed sequence tag (EST) projects are rapidly cataloging and cloning the genes of higher organisms, including humans. The emerging challenge is to uncover the functional roles of the genes and to quickly identify gene products with desired properties. The growing collection of gene sequences and cloned cDNAs demands the development of systematic and high-throughput approaches to characterizing the gene products. The uses of DNA microarrays for transcriptional profiling and of yeast two-hybrid arrays for determining protein-protein interactions are recent examples of genomic approaches to the characterization of gene products (Schena, M. et al., *Nature*, 10:623 (2000)). Comparable strategies do not exist to analyze the function, within mammalian cells, of large sets of genes. Currently, in vivo gene analysis can be done—on a gene-by-gene scale—by transfecting cells with a DNA construct that directs the overexpression of the gene product or inhibits its expression or function. The effects on cellular physiology of altering the level of a gene product is then detected using a variety of functional assays.

A variety of DNA transfection methods, such as calcium phosphate coprecipitation, electroporation and cationic liposome-mediated transfection (e.g., lipofection) can be used to introduce DNA into cells and are useful in studying gene regulation and function. Additional methods, particularly high throughput assays that can be used to screen large sets of DNAs to identify those encoding products with properties of interest, would be useful to have available.

SUMMARY OF THE INVENTION

The present invention provides a strategy for high throughput analysis of gene function in cells. One aspect of the present invention provides methods and reagents for creating transfected cell microarrays that are suitable for rapidly screening large sets of nucleic acid constructs for those encoding desired products or for causing cellular phenotypes of interest is described. For instance, a spatially defined array of nucleic acids, such as expression vectors, is used to generate a spatially defined array of transfected cells. The cells can be screened for the ability of a transfected nucleic acid to confer a particular phenotype on the cell, and, by reference to the position of the cell(s) on the array, the identity of the nucleic acid can be determined.

Accordingly, the present invention relates to a method, referred to as a reverse transfection method, in which a defined nucleic acid (a nucleic acid of known sequence or source), also referred to as a nucleic acid of interest or a nucleic acid to be introduced into cells, is introduced into cells in defined areas of a lawn of eukaryotic cells, in which it will be expressed or will itself have an effect on or interact with a cellular component or function. Any suitable nucleic acid such as an oligonucleotide, DNA and RNA can be used in the methods of the present invention. The particular embodiments of the invention are described in terms of DNA. However, it is to be understood that any suitable nucleic acid is encompassed by the present invention.

In one embodiment, the present invention relates to a method in which defined DNA (DNA of known sequence or source), also referred to as DNA of interest or DNA to be introduced into cells, is introduced into cells in defined areas of a lawn of eukaryotic cells, in which it will be expressed or will itself have an effect on or interact with a cellular component or function. In the method, a mixture, defined below, comprising DNA of interest (such as cDNA or genomic DNA incorporated in an expression vector) and a carrier protein is deposited (e.g., spotted or placed in small defined areas) onto a surface (e.g., a slide or other flat surface, such as the bottoms of wells in a multi-welled plate) in defined, discrete (distinct) locations and allowed to dry, with the result that the DNA-containing mixture is affixed to the surface in defined discrete locations.

Such locations are referred to herein, for convenience, as defined locations. The DNA-containing mixture can be deposited in as many discrete locations as desired. The resulting product is a surface bearing the DNA-containing mixture in defined discrete locations; the identity of the DNA present in each of the discrete locations (spots) is known/defined. Eukaryotic cells, such as mammalian cells (e.g., human, monkey, canine, feline, bovine, or murine cells), bacterial, insect, or plant cells, are plated (placed) onto the surface bearing the DNA-containing mixture in sufficient density and under appropriate conditions for introduction/entry of the DNA into the eukaryotic cells and expression of the DNA or its interaction with cellular components. Preferably, the eukaryotic cells (in an appropriate medium) are plated on top of the dried DNA-containing spots at high density (e.g., $1\times10^5/cm^2$) in order to increase the likelihood that reverse transfection will occur. The DNA present in the DNA-containing mixture affixed to the surface enters eukaryotic cells (reverse transfection occurs) and is expressed in the resulting reverse transfected eukaryotic cells.

In one embodiment of the method, referred to as a "gelatin-DNA" embodiment, the DNA-containing mixture, referred to herein as a gelatin-DNA mixture, comprises DNA (e.g., DNA in an expression vector) and gelatin, which is present in an appropriate solvent, such as water or double deionized water. The mixture is spotted onto a surface, such as a slide, thus producing a surface bearing (having affixed thereto) the gelatin-DNA mixture in defined locations. The resulting product is allowed to dry sufficiently that the spotted gelatin-DNA mixture is affixed to the slide and the spots remain in the locations to which they have become affixed, under the conditions used for subsequent steps in the method. For example, a mixture of DNA in an expression vector and gelatin is spotted onto a slide, such as a glass slide coated with Σ poly-L-lysine (e.g., Sigma, Inc.), for example, by hand or using a microarrayer. The DNA spots can be affixed to the slide by, for example, subjecting the resulting product to drying at room temperature, at elevated temperatures or in a vacuum-dessicator. The length of time necessary for sufficient drying to occur depends on several factors, such as the quantity of mixture placed on the surface and the temperature and humidity conditions used.

The concentration of DNA present in the mixture will be determined empirically for each use, but will generally be in the range of from about 0.01 $\mu g/\mu l$ to about 0.2 $\mu g/\mu l$ and, in specific embodiments, is from about 0.02 $\mu g/\mu l$ to about 0.10 $\mu g/\mu l$. Alternatively, the concentration of DNA present in the mixture can be from about 0.01 $\mu g/\mu l$ to about 0.5 $\mu g/\mu l$, from about 0.01 $\mu g/\mu l$ to about 0.4 $\mu g/\mu l$ and from about 0.01 $\mu g/\mu l$ to about 0.3 $\mu g/\mu l$. Similarly, the concentration of gelatin, or another carrier macromolecule, can be determined empirically for each use, but will generally be in the range of 0.01% to 0.5% and, in specific embodiments, is from about 0.05% to about 0.5%, from about 0.05% to about 0.2% or from about 0.1% to about 0.2%. The final concentration of DNA in the mixture (e.g., DNA in gelatin) will generally be from about 0.02 $\mu g/\mu l$ to about 0.1 $\mu g/\mu l$ and in a specific embodiment described herein, DNA is diluted in 0.2% gelatin (gelatin in water) to produce a final concentration of DNA equal to approximately 0.05 $\mu g/\mu l$.

If the DNA used is present in a vector, the vector can be of any type, such as a plasmid or viral-based vector, into which DNA of interest (DNA to be expressed in reverse transfected cells) can be introduced and expressed (after reverse transfection) in recipient cells. For example, a CMV-driven expression vector can be used. Commercially available plasmid-based vectors, such as pEGFP (Clontech) or pcDNA3 (Invitrogen), or viral-based vectors can be used. In this embodiment, after drying of the spots containing the gelatin-DNA mixture, the surface bearing the spots is covered with an appropriate amount of a lipid-based transfection reagent and the resulting product is maintained (incubated) under conditions appropriate for complex formation between the DNA in the spots (in the gelatin-DNA mixture) and the lipid-based transfection reagent. In one embodiment, the resulting product is incubated for approximately 20 minutes at 25° C. Subsequently, transfection reagent is removed, producing a surface bearing DNA (DNA in complex with transfection reagent), and cells in an appropriate medium are plated onto the surface. The resulting product (a surface bearing DNA and plated cells) is maintained under conditions that result in entry of the DNA into plated cells.

A second embodiment of the method is referred to as a "lipid-DNA" embodiment. In this embodiment, a DNA-containing mixture (referred to herein as a lipid-DNA mixture) which comprises DNA (e.g., DNA in an expression vector); a carrier protein (e.g., gelatin); a sugar, such as sucrose; a buffer that facilitates DNA condensation and an appropriate lipid-based transfection reagent is spotted onto a surface, such as a slide, thus producing a surface bearing the lipid-DNA mixture in defined locations. The resulting product is allowed to dry sufficiently that the spotted lipid-DNA mixture is affixed to the slide and the spots remain in the locations to which they have become affixed, under the conditions used for subsequent steps in the method. For example, a lipid-DNA mixture is spotted onto a slide, such as a glass slide coated with $\Sigma$poly-L-lysine (e.g., Sigma, Inc.), for example, by hand or using a microarrayer. The DNA spots can be affixed to the slide as described above for the gelatin-DNA method.

The concentration of DNA present in the mixture will be determined empirically for each use, but will generally be in the range of 0.5 $\mu g/\mu l$ to 1.0 $\mu g/\mu l$. A range of sucrose concentrations can be present in the mixture, such as from about 0.1M to about 0.4M. Similarly, a range of gelatin concentrations can be present in the mixture, such as from about 0.01% to about 0.05%. In this embodiment, the final concentration of DNA in the mixture will vary and can be determined empirically. In specific embodiments, final DNA concentrations range from about 0.1 $\mu g/\mu l$ to about 2.0 $\mu g/\mu l$.

If a vector is used in this embodiment, it can be any vector, such as a plasmid, or viral-based vector, into which DNA of interest (DNA to be expressed in reverse transfected cells) can be introduced and expressed (after reverse transfection), such as those described for use in the gelatin-DNA embodiment.

After drying is complete (has occurred to a sufficient extent that the DNA remains affixed to the surface under the conditions used in the subsequent steps of the method), eukaryotic cells into which the DNA is to be reverse transfected are placed on top of the surfaces onto which the DNA-containing mixture has been affixed. Actively growing cells are generally used and are plated, preferably at high density (such as $1 \times 10^5/cm^2$), on top of the surface containing the affixed DNA-containing mixture in an appropriate medium, such as Dulbecco's Modified Eagles Medium (DMEM) containing 10% heat-inactivated fetal serum (IFS) with L-glutamine and penicillin/streptomycin (pen/strep). Other media can be used and their components can be determined based on the type of cells to be transfected. The resulting slides, which contain the dried lipid-DNA mixture and cells into which the DNA is to be reverse transfected, are maintained under conditions appropriate for growth of the cells and entry of DNA, such as an entry of an expression vector containing the DNA, into cells. In the present method, approximately one to two cell cycles are sufficient for reverse transfection to occur, but this will vary with the cell type and conditions used and the appropriate length of time for a specific combination can be determined empirically. After sufficient time has elapsed, slides are assessed for reverse transfection (entry of DNA into cells) and expression of the encoded product or effect of the introduced DNA on reverse-transfected cells, using known methods. This can be done, for example, by detecting immunofluorescence or enzyme immunocytochemistry, autoradiography, in situ hybridization, or other means of detecting expression of the DNA or an effect of the encoded product or of the DNA itself on the cells into which it is introduced. If immunofluorescence is used to detect expression of an encoded protein, an antibody that binds the protein and is fluorescently labeled is used (e.g., added to the slide under conditions suitable for binding of the antibody to the protein) and the location (spot or area of the surface) containing the protein is identified by detecting fluorescence. The presence of fluorescence indicates that reverse transfection has occurred and the encoded protein has been expressed in the defined location(s) which show fluorescence. The presence of a signal, detected by the method used, on the slides indicates that reverse transfection of the DNA into cells and expression of the encoded product or an effect of the DNA in recipient cells has occurred in the defined location(s) at which the signal is detected. As described above, the identity of the DNA present at each of the defined locations is known; thus, when expression occurs, the identity of the expressed protein is also known.

Thus, the present invention relates, in one embodiment, to a method of expressing defined DNA, such as cDNA or genomic DNA, in defined locations or areas of a surface onto which different DNAs, such as DNA in a vector, such as an expression vector, has been affixed, as described herein. Because each area of the surface has been covered/spotted with DNA of known composition, it is a simple matter to identify the expressed protein. In addition, the present method is useful to identify DNAs whose expression alters (enhances or inhibits) a pathway, such as a signaling pathway in a cell or another property of a cell, such as its morphology or pattern of gene expression. The method is particularly useful, for example, as a high-throughput screening method, such as in a microarray format. It can be used in this format for identifying DNAs whose expression changes the phosphorylation state or subcellular location of a protein of interest or the capacity of the cell to bind a reagent, such as a drug or hormone ligand. In a second embodiment, which is also useful as a high-throughput screening method, DNA reverse transfected into cells has an effect on cells or interacts with a cellular component(s) without being expressed, such as through hybridization to cellular nucleic acids or through antisense activity.

Also the subject of this invention are arrays, including microarrays, of defined DNAs spotted onto (affixed to) a surface and array: including microarrays of reverse transfected cells spotted to (affixed to) a surface by the method described herein. Such arrays can be produced by the gelatin-DNA embodiment or the lipid-DNA embodiment of the present method. Arrays of this invention are surfaces, such as slides (e.g., glass or Σ poly-L-lysine coated slides) or wells, having affixed thereto (bearing) in discrete, defined locations DNAs, such as cDNAs or genomic DNA, or cells containing DNA of interest introduced into the cells by the reverse transfection method described herein.

A method of making arrays of the present invention is also the subject of this invention. The method comprises affixing DNAs or reverse transfected cells onto a surface by the steps described herein for the gelatin-DNA embodiment or the lipid-DNA embodiment.

A DNA array of the present invention comprises a surface having affixed thereto, in discrete, defined locations, DNA of known sequence or source by a method described herein. In one embodiment, DNA is affixed to a surface, such as a slide, to produce an array (e.g., a macro-array or a micro-array) by spotting a gelatin-DNA mixture, as described herein, onto the surface in distinct, defined locations (e.g., by hand or by using an arrayer, such as a micro-arrayer) and allowing the resulting surface bearing the gelatin-DNA mixture to dry sufficiently that the spots remain affixed to the surface under conditions in which the arrays are used. In an alternative embodiment, DNA is affixed to a surface, such as a slide, to produce an array by spotting a lipid-DNA mixture, as described herein, onto the surface in distinct defined locations (e.g., by hand or by using an arrayer, such as a micro-arrayer) and allowing the resulting surface bearing the lipid-DNA mixture to dry sufficiently that the spots remain affixed to the surface under the conditions in which the arrays are used. This results in production of a surface bearing (having affixed thereto) DNA-containing spots.

An array of reverse transfected cells can also be produced by either embodiment described herein. In the gelatin-DNA embodiment, the steps described above for producing DNA arrays are carried out and subsequently, the surface bearing the DNA-containing spots is covered with an appropriate amount of a lipid-based transfection reagent and the resulting product is maintained (incubated) under conditions appropriate for complex formation between DNA in the spots and the reagent. After sufficient time (e.g., about 20 minutes at 25° C.) for complex formation to occur, transfection reagent is removed, producing a surface bearing DNA and cells in an appropriate medium are added. The resulting product (a surface bearing DNA and plated cells) is maintained under conditions that result in entry of DNA into plated cells, thus producing an array (a surface bearing an array) of reverse transfected cells that contain defined DNA and are in discrete, defined locations on the array. Such cell arrays are the subject of this invention.

In the lipid-DNA embodiment, the steps described above for producing DNA arrays are carried out and subsequently (after drying is sufficient to affix the DNA-containing spots to the surface, such as a slide or well bottom), cells are plated on top of the surface bearing the DNA-containing spots and the resulting slides, which contain the dried lipid-DNA mixture and cells to be reverse transfected, are maintained under conditions appropriate for growth of the cells and entry of DNA into the cells, thus producing an array (a surface bearing an array) of reverse transfected cells that contain defined DNA and are in discrete, defined locations on the array. Such arrays are the subject of this invention.

The secondary antibody used was Cy3 µg/ml labeled anti-mouse antibody (Jackson Immunoresearch) at 3.1 µg/ml for 40 minutes at room temperature. Panels labeled Cy3 and GFP show location of clusters expressing HA-GST and GFP, respectively.

Merged panel shows superimposition of Cy3 and GFP signals and yellow color indicates co-expression. Scale bar equals 100 µm.

Figure 1:
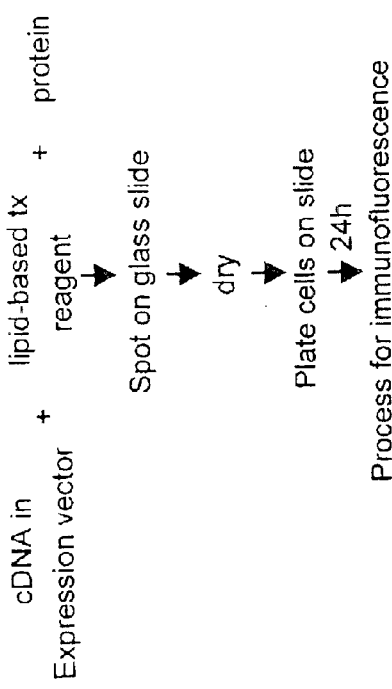
FIG. 1 is a schematic representation of one embodiment of the present method of reverse transfection, in which cDNA (HA-GST, HA-FKBP12 or myc-FRB) in an expression vector (prk5) was introduced into cells by the following procedures: combining cDNA in an expression vector, a lipid-based transfection reagent and a carrier protein, to produce a mixture; spotting the mixture onto a glass slide; allowing the spotted mixture to dry on the slide surface; plating human embryonic kidney (HEK 293T) cells into which cDNA is to be introduced onto the slide; maintaining the resulting slide under conditions appropriate for reverse transfection to occur; and detecting immunofluorescence using a fluorescently labeled antibody that binds HA but not myc, demonstrating the presence and location of expressed cDNA.
Figure 1:
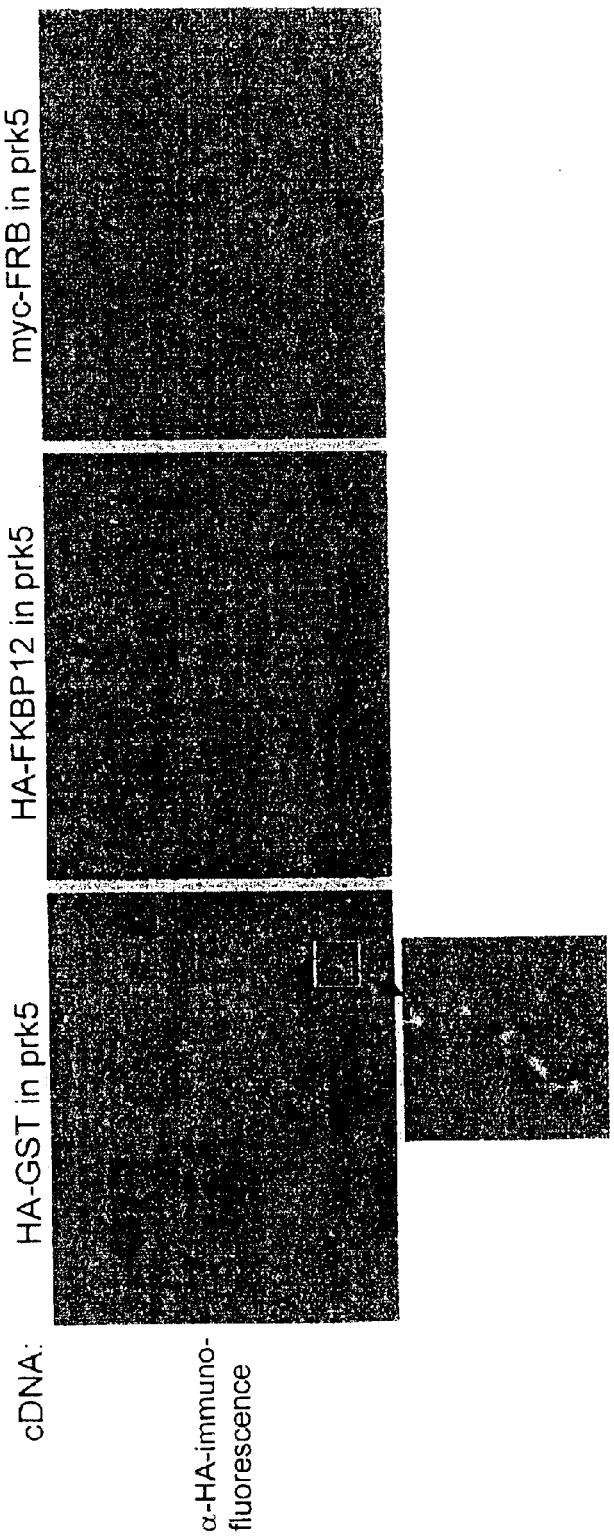
Figure 2:
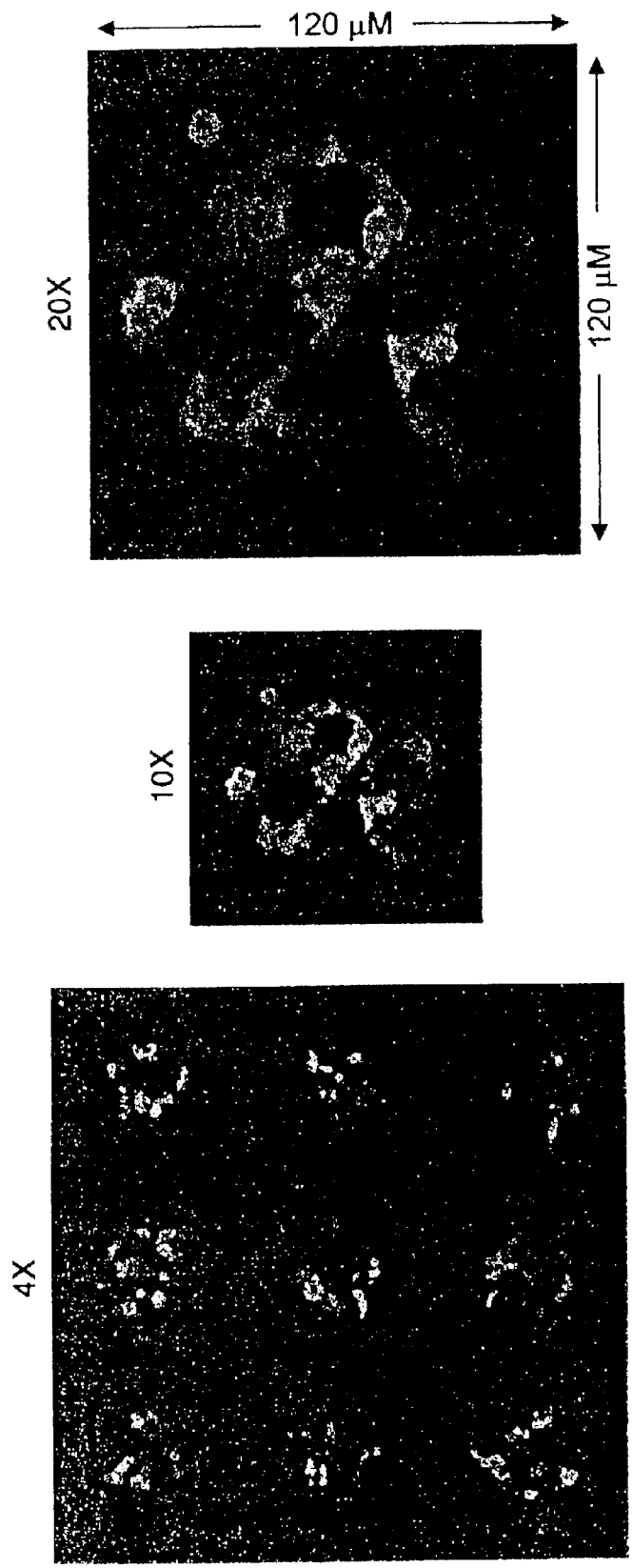
FIG. 2 shows the results of reverse transfection of HEK293T cells with HA-GST, as demonstrated using anti-HA immunofluorescence.
Figure 3:
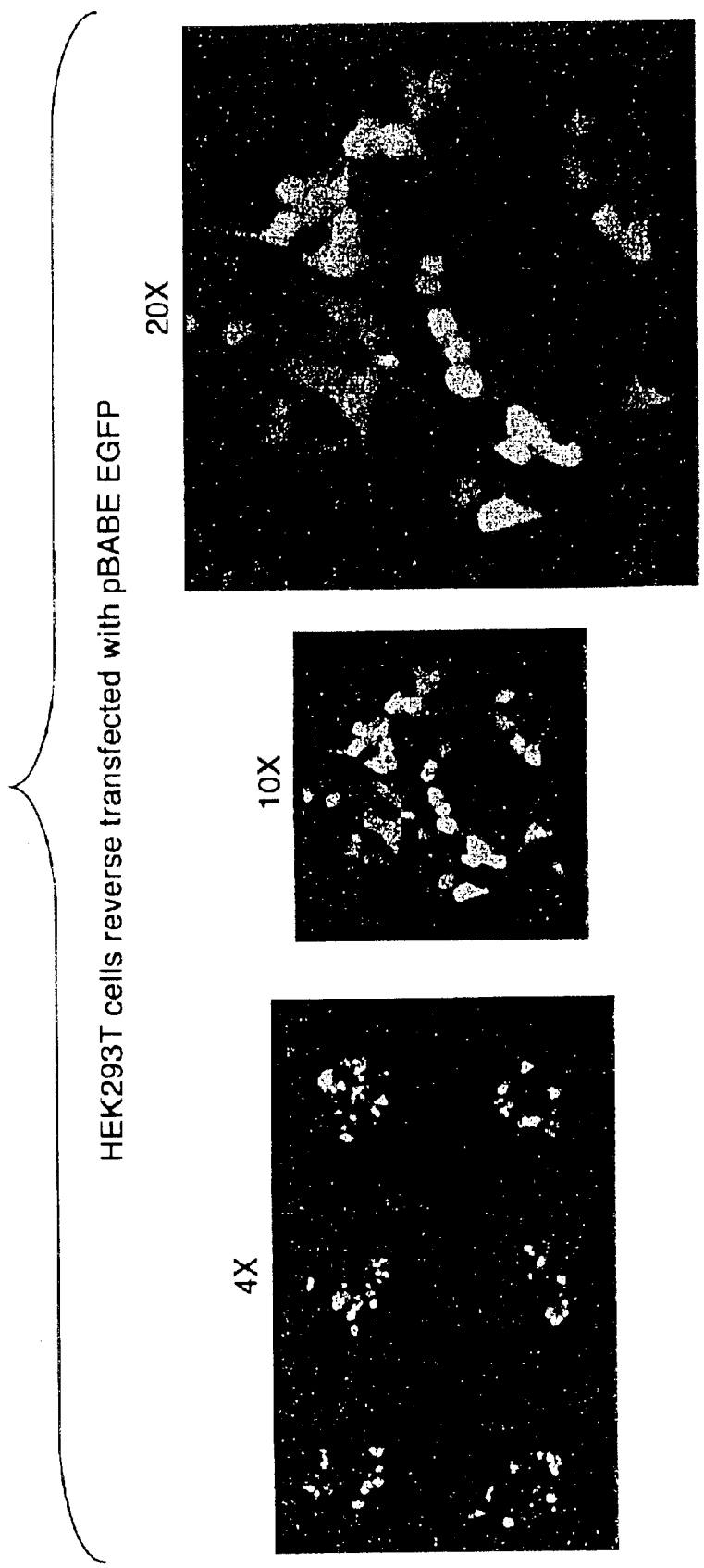
FIG. 3 shows the results of reverse transfection of HEK293T cells with pBABE EGFP, as demonstrated by detecting endogenous fluorescence of EGFP.
Figure 4A:
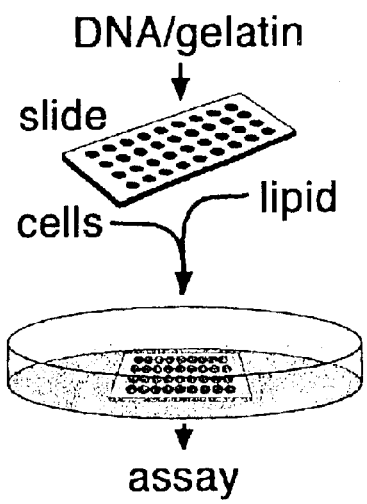
FIG. 4A is a schematic for making transfected cell microarrays using a well-less transfection of plasmid DNAs in defined areas of a lawn of mammalian cells. Plasmid DNA dissolved in an aqueous gelatin solution is printed on a glass slide using a robotic arrayer. The slide is dried and the printed array covered with a lipid transfection reagent. After removal of the lipid, the slide is placed in a culture dish and covered with cells in media. The transfected cell microarray forms in 1–2 days and is then ready for downstream assays. An alternative method in which the lipid is added to the DNA/gelatin solution prior to printing is also described.
Figure 4B:
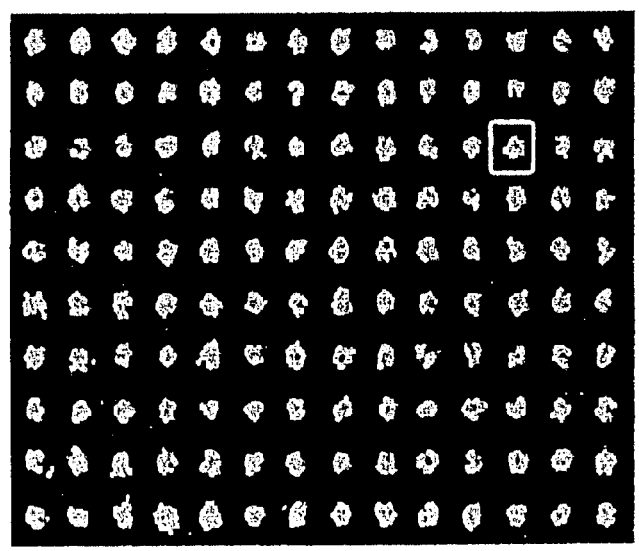
FIG. 4B is a GFP-expressing microarray made from a slide printed in a 12×8 pattern with a GFP expression construct.
Figure 4C:
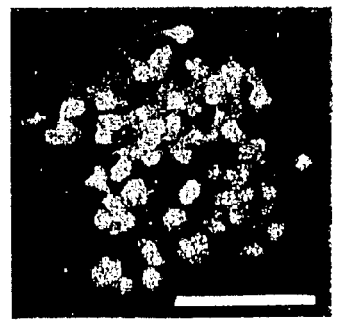
FIG. 4C is a higher magnification image obtained with fluorescence microscopy of the cell cluster boxed in FIG. 4B. Scale bar equals 100 μm.
Figure 4D:
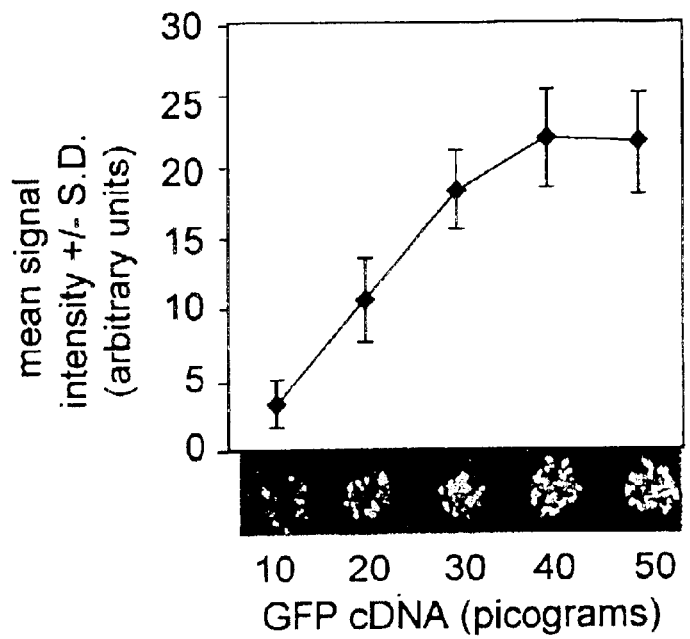
FIG. 4D is a graph of GFP cDNA (picograms) versus mean signal intensity +/−S.D. showing expression levels of clusters in a transfected cell microarray are proportional, over a four-fold range, to the amount of plasmid DNA printed on the slide. Arrays were printed with elements containing the indicated amounts of the GFP construct. Amount of DNA assumes a one nanoliter printing volume. After transfection, the mean +/−S.D. of the fluorescence intensities of the cell clusters was determined. Arrays were prepared as described in Example 3 except that the concentration of the GFP expression plasmid was varied from 0.010–0.050 μg/μl while the total DNA concentration was kept constant at 0.050 μg/μl with empty vector (prk5). Cell clusters were photographed and the signal intensity quantitated with Image Quant (Fuji). The fluorescent image is from a representative experiment.
Figure 4E:
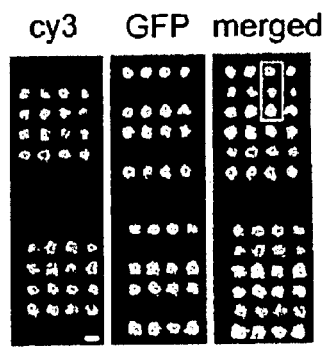
FIG. 4E is a scan image showing that by printing mixtures of two plasmids, cotransfection is possible with transfected cell microarrays. Arrays with elements containing expression constructs for HA-GST, GFP or both were transfected and processed for anti-myc immunofluorescence. For immunofluorescence staining the cells were fixed as described in Example 3, permeabilized in 0.1% TRITON X-100 (polyoxyethylene (10) isooctylphenyl ether) in PBS for 15 minutes at room temperature and probed with primary and secondary antibodies as described. Primary antibodies were used for 1 hour at room temperature at the following concentrations: 1:500 anti-HA ascites (BaBCo), 2 µg/ml anti-myc 9E-10 (Calbiochem), 2 µg/ml anti-V5 (Invitrogen), or 10 µg/ml 4G10 anti-phosphotyrosine (Upstate Biotechnologies).
Figure 4F:

FIG. 4F is an enlarged view of boxed area of scan image from FIG. 4E.

Figure 5A:
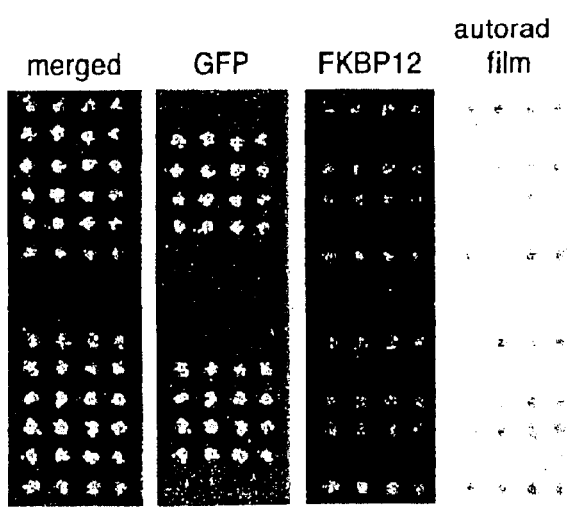

FIG. 5A is a laser scan showing detection of the receptor for FK506. Arrays with elements containing expression constructs for GFP, myc-FKBP12 or both were printed and transfected with HEK293 cells. 5 nM dihydro-FK506 [propyl-$^3$H] (NEN) was added to the culture media 1 hour prior to fixation and processing for immunofluorescence and autoradiography. Slides were process for anti-myc immunofluorescence, scanned at 5%m resolution and photographed using a fluorescent microscope, and then exposed to tritium sensitive film (HYPERFILM, Amersham) for 4 days. Autoradiographic emulsion was performed as described by the manufacturer (Amersham). Laser scans show expression pattern of GFP and FKBP12 and superimposition of both (merged). Film autoradiography detects binding of tritiated FK506 to the same array (autorad film).

Figure 5B:

FIG. 5B is a higher magnification image obtained by fluorescent microscopy of an FKBP12-expressing cluster (FKBP12). Emulsion autoradiography detects, with cellular resolution, binding of tritiated FK506 to the same cluster (autorad emulsion).

Figure 5C:
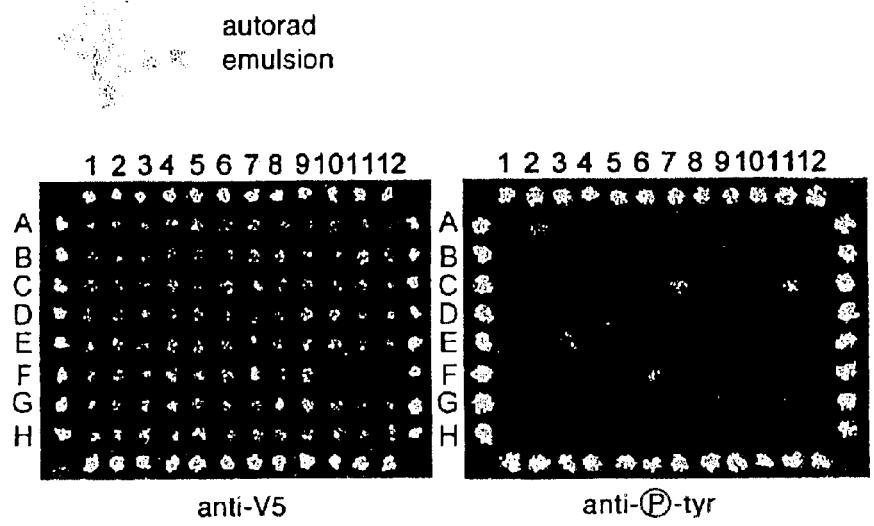

FIG. 5C is a scan showing detected components of tyrosine kinase signaling cascades. 192 V5-epitope-tagged cDNAs in expression vectors were printed in two 8×12 subgrids named array 1 and 2. For ease of determining the coordinates of cell clusters within the arrays a border around each array was printed with the GFP expression construct. After transfection, separate slides were processed for anti-V5 or anti-phosphotyrosine immunofluorescence and Cy3 and GFP fluorescence detected. Merged images of array 1 show location of clusters expressing V5-tagged proteins (left panel) and having increased levels of phosphotyrosine (right panel). No DNA was printed in coordinates F10–12.

Figure 5D:
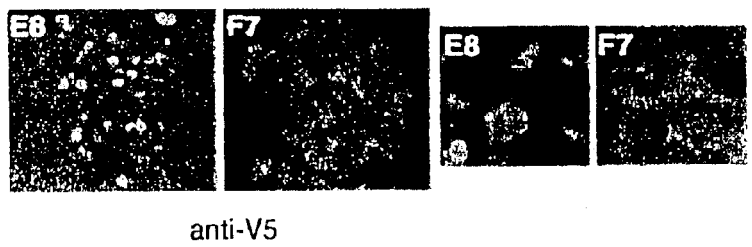

FIG. 5D show two examples of the morphological phenotypes detectable in the transfected cell microarrays described in FIG. 5C. Clusters shown are E8 and F7 from array 2.

Figure 6:
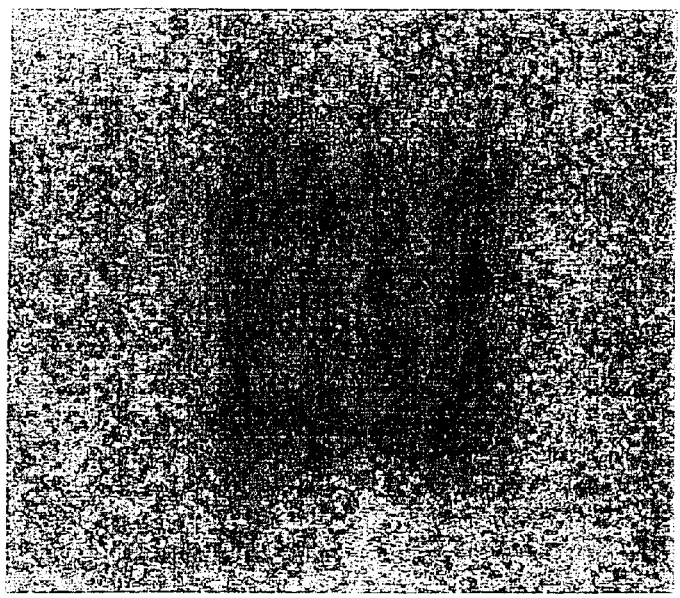

FIG. 6 shows a transfection array that has been transferred to a nitrocellulose filter.

DETAILED DESCRIPTION OF THE INVENTION

I. Overview

The growing collection of gene sequences and cloned cDNAs demands the development of systematic and high-throughput approaches to characterizing the gene products. The uses of DNA microarrays for transcriptional profiling and of two-hybrid assays for determining protein-protein interactions are recent examples of genomic approaches to the characterization of gene products. Comparable strategies have not previously existed to analyze the function, particularly within mammalian cells, of large sets of genes. Currently, in vivo analysis can be done, on a gene-by-gene scale, by expressing with cells a nucleic acid construct that directs the overexpression of a gene product or inhibits its synthesis or function.

The present invention relates to a microarray-driven gene expression system for the functional analysis of many gene products in parallel. Cells are cultures on a solid surface printed in defined locations with different nucleic acid constructs which can be taken up by the cells. The effects on cellular physiology by the product of the transfection array can be detected. Rather than having to recover the transfected construct to ascertain its identity, the identity is determined by the position of the transfectant of interest on the array. The subject assay can be particular useful where cell is the read-out used to identify a construct of interest.

A microarray-based system was developed to analyze the function in cells of many genes in parallel. Cells are cultured on a glass slide printed in defined locations with solutions containing different DNAs. Cells growing on the printed areas take up the DNA, creating spots of localized transfection within a lawn of non-transfected cells. By printing sets of complementary DNAs (cDNAs) cloned in expression vectors, micoarrays which comprise groups of live cells that express a defined cDNA at each location can be made. Transfected cell microarrays can be of broad utility for the high-throughput expression cloning of genes, particularly in areas such as signal transduction and drug discovery. For example, as shown herein, transfected cell microarrays can be used for the unambiguous identification of the receptor for the immunosuppressant FK506 and components of tyrosine kinase pathways.

The present invention relates to a method of introducing defined DNAs into cells at specific discrete, defined locations on a surface by means of a reverse transfection method. That is, the present method makes use of DNAs, of known sequence and/or source, affixed to a surface (DNA spots), such as a slide or well bottom, and growing cells that are plated onto the DNA spots and maintained under conditions appropriate for entry of the DNAs into the cells. The size of the DNA spots and the quantity (density) of the DNA spots affixed to the surface can be adjusted depending on the conditions used in the methods. For example, the DNA, spots can be from about 100 µm to about 200 µm in diameter and can be affixed from about 200 µm to about 500 µm apart on the surface. The present method further includes identification or detection of cells into which DNA has been reverse transfected. In one embodiment, DNA introduced into cells is expressed in the cells, either by an expression vector containing the DNA or as a result of integration of reverse transfected DNA into host cell DNA, from which it is expressed. In an alternative embodiment of the present method, DNA introduced into cells is not expressed, but affects cell components and/or function itself. For example, antisense DNA can be introduced into cells by this method and affect cell function. For example, a DNA fragment which is anti-sense to an mRNA encoding a receptor for a drug can be introduced into cells via reverse transfection. The anti-sense DNA will decrease the expression of the drug receptor protein, causing a decrease in drug binding to cells containing the anti-sense DNA. In the method, a mixture comprising DNA of interest (such as cDNA or genomic DNA incorporated in an expression vector) and a carrier protein is deposited (e.g., spotted or placed in small defined areas) onto a surface (e.g., a slide or other flat surface, such as the bottoms of wells in a multi-welled plate) in defined, discrete (distinct) locations and allowed to dry, with the result that the DNA-containing mixture is affixed to the surface in defined discrete locations.

Detection of effects on recipient cells (cells containing DNA introduced by reverse transfection) can be carried out by a variety of known techniques, such as immunofluorescence, in which a fluorescently labeled antibody that binds a protein of interest (e.g., a protein thought to be encoded by a reverse transfected DNA or a protein whose expression or function is altered through the action of the reverse transfected DNA) is used to determine if the protein is present in cells grown on the DNA spots.

The methods of this invention are useful to identify DNAs of interest (DNAs that are expressed in recipient cells or act upon or interact with recipient cell constituents or function, such as DNAs that encode a protein whose function is desired because of characteristics its expression gives cells in which it is expressed). They can be used in a variety of formats, including macro-arrays and micro-arrays. They permit a DNA array to be converted into a protein or cell array, such as a protein or cell microarray.

II. Definitions

Before further description of the invention, certain terms employed in the specification, examples and appended claims are, for convenience, collected here.

As used herein, the term "nucleic acid" refers to polynucleotides such as deoxyribonucleic acid (DNA), and, where appropriate, ribonucleic acid (RNA).

"Complementary DNA" or a "cDNA" as used herein includes recombinant genes synthesized by reverse transcription of mRNA and from which intervening sequences (introns) have been removed.

As used herein, the terms "heterologous nucleic acid" and "foreign nucleic acid" refer to a nucleic acid, e.g., DNA or RNA, that does not occur naturally as part of the genome in which it is present or which is found in a location or locations in the genome that differs from that in which it occurs in nature. Heterologous DNA is not endogenous to the cell into which it is introduced, but has been obtained from another cell. Examples of heterologous nucleic acid include, but are not limited to, DNA that encodes test polypeptides, receptors, reporter genes, transcriptional and translational regulatory sequences, selectable or traceable marker proteins, such as a protein that confers drug resistance. Examples of heterologous RNA include, but are not limited to, anti-sense RNA sequences, ribozymes, and double-stranded RNA (for inducing sequence-specific RNA interference).

As used herein, the terms "target nucleic acid" and "target sequence" refer to the component of a transfection array, e.g., the portion or portions of a nucleic acid being transfected into the host cells, which is of interest with respect to its ability to confer a change in the phenotype of the host cells. In general, though not always, the target nucleic acid will that portion(s) of the nucleic acid of the transfection array that is varied from one portion of the array to the next. The target nucleic acid can be a coding sequence for a protein, a "coding" sequence for an RNA molecule (e.g., which is transcribed into an anti-sense RNA sequence, a ribozyme or double-stranded RNA), or a regulatory sequence (e.g., as part of a reporter construct), to name but a few examples.

The term "feature," as it is used in describing a transfection array, refers to an area of a substrate having a homogenous collection of a target sequence (or sequences in the case of certain co-transfection embodiments). One feature is different than another feature if the target sequences of the different features have different nucleotide sequences.

The term "loss-of-function," as it refers to the effect of a target sequence, refers to those target sequences which, when expressed in a host cell, inhibit expression of a gene or otherwise render the gene product thereof to have substantially reduced activity, or preferably no activity relative to one or more functions of the corresponding wild-type gene product.

As used herein, a "desired phenotype" refers to a particular phenotype for that the user of the subject method seeks to have selectively conferred on the host cell line upon expression of a target sequence.

As used herein, the term "vector" refers to a nucleic acid molecule capable of being transporting into and/or maintained within a cell. Preferred vectors are those capable of autonomous replication. In the present specification, "plasmid" and "vector" are used interchangeably as the plasmid is the most commonly used form of vector.

As used herein, the term "operatively linked" refers to the functional relationship of a nucleic acid sequence with regulatory and effector nucleotide sequences, such as promoters, enhancers, transcriptional and translational start and stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to, and transcribes the DNA.

As used herein, the term "expression" refers to any number of steps comprising the process by which polynucleic acids are transcribed into RNA, and (optionally) translated into peptides, polypeptides, or proteins. If the polynucleic acid is derived from genomic DNA, expression may, if an appropriate eukaryotic host cell or organism is selected, include splicing of the RNA.

As used herein, "recombinant cells" include any cells that have been modified by the introduction of heterologous nucleic acid. Control cells include cells that are substantially identical to the recombinant cells, but do not express one or more of the proteins encoded by the heterologous nucleic acid.

The terms "protein," "polypeptide," and "peptide" are used interchangeably herein.

The terms "recombinant protein," "heterologous protein," and "exogenous protein" are used interchangeably throughout the specification and refer to a polypeptide which is produced by recombinant DNA techniques, wherein generally, DNA encoding the polypeptide is inserted into a suitable expression vector which is in turn used to transform a host cell to produce the heterologous protein. That is, the polypeptide is expressed from a heterologous nucleic acid.

As used herein, "cell surface receptor" refers to molecules that occur on the surface of cells, interact with the extracellular environment, and transmit or transduce the information regarding the environment intracellularly in a manner that may modulate intracellular second messenger activities or transcription of specific promoters, resulting in transcription of specific genes.

As used herein, "extracellular signals" include a molecule or a change in the environment that is transduced intracellularly via cell surface proteins that interact, directly or indirectly, with the signal. An extracellular signal or effector molecule includes any compound or substance that in some manner alters the activity of a cell surface protein. Examples of such signals include, but are not limited to, molecules such as acetylcholine, growth factors and hormones, lipids, sugars and nucleotides that bind to cell surface and/or intracellular receptors and ion channels and modulate the activity of such receptors and channels. The term also includes as yet unidentified substances that modulate the activity of a cellular receptor, and thereby influence intracellular functions. Such extracellular signals are potential pharmacological agents that may be used to treat specific diseases by modulating the activity of specific cell surface receptors.

"Orphan receptors" is a designation given to a receptors for which no specific natural ligand has been described and/or for which no function has been determined.

As used herein, a "reporter gene construct" is a nucleic acid that includes a "reporter gene" operatively linked to at least one transcriptional regulatory sequence. Transcription of the reporter gene is controlled by these sequences to which they are linked. The activity of at least one or more of these control sequences is directly or indirectly regulated by the target receptor protein. Exemplary transcriptional control sequences are promoter sequences. A reporter gene is meant to include a promoter-reporter gene construct which is heterologously expressed in a cell.

"Signal transduction" is the processing of physical or chemical signals from the cellular environment through the cell membrane, and may occur through one or more of several mechanisms, such as activation/inactivation of enzymes (such as proteases, or other enzymes which may alter phosphorylation patterns or other post-translational modifications), activation of ion channels or intracellular ion stores, effector enzyme activation via guanine nucleotide binding protein intermediates, formation of inositol phosphate, activation or inactivation of adenylyl cyclase, direct activation (or inhibition) of a transcriptional factor and/or activation.

The term "modulation of a signal transduction activity of a receptor protein" in its various grammatical forms, as used herein, designates induction and/or potentiation, as well as inhibition of one or more signal transduction pathways downstream of a receptor.

The term "autocrine cell," as used herein, refers to a cell which produces a substance which can induce a phenotypic response within the same cell as produces the substance.

III. Transfection Arrays

The target nucleic acid used in the transfection arrays of the present invention can be, for example, DNA, RNA or modified or hybrid forms thereof. The target nucleic acid may be from any of a variety of sources, such as nucleic acid isolated from cells, or that which is recombinantly produced or chemically synthesized.

For example, the transfection array can include coding sequence from cDNAs or genomic DNA. In addition to native sequences, the coding sequences can include those which have been mutated relative to the native sequence, e.g., a coding sequence that differs from a naturally occurring sequence by deletion, substitution or addition of at least one residue. It can correspond to full length or partial sequences, can be antisense in orientation, or can represent a non-coding sequence.

In other embodiments, all or a portion of the target nucleic acid sequence can be synthesized chemically. In such a manner, random and semi-random sequence can be introduced into the target sequences, as well as modified forms of nucleotides and nucleotide linkages, such as the use of modified backbones, methylated nucleotides and the like.

The target nucleic acid sequences can be present as part of a larger vector, such as an expression vector (e.g., a plasmid or viral-based vector), but it need not be. The nucleic acid of the array can be introduced into cells in such a manner that at least the target sequence becomes integrated into the genomic DNA and is expressed, or the target sequence remains extrachromosomal (e.g., is maintained episomally).

The nucleic acid for use in the transfection arrays of the present invention can be linear or circular, double stranded or single stranded, and can be of any size. In certain preferred embodiments, especially where traditional expression vectors are used, the target sequence is from about 200 nt to about 10 kb in size, more preferably from about 200 nt to about 5 kb, and even more preferably 200 nt to 2 kb. In such embodiments, the arrayed nucleic acid, e.g., which includes the target sequence, can be from about 1 kb to about 15 kb, and more preferably from about 5 kb to about 8 kb.

In certain preferred embodiments, the transfection array is made up of a variegated library of expression vectors. Ligating a polynucleotide coding sequence or other transcribable sequences an expression vector can be carried out using standard procedures. Similar procedures, or modifications thereof, can be readily employed to prepare arrays of expression vectors in accord with the subject invention.

In general, it will be desirable that the vector be capable of replication in the host cell. It may be a DNA which is integrated into the host genome, and thereafter is replicated as a part of the chromosomal DNA, or it may be DNA which replicates autonomously, as in the case of a episomal plasmid. In the latter case, the vector will include an origin of replication which is functional in the host. In the case of an integrating vector, the vector may include sequences which facilitate integration, e.g., sequences homologous to host sequences, or encoding integrases. The use of retroviral long terminal repeats (LTR) or adenoviral inverted terminal repeats (ITR) in the construct of the transfection array can, for example, facilitate the chromosomal integration of the construct.

Appropriate cloning and expression vectors for use with bacterial, fungal, yeast, and mammalian cellular hosts are known in the art, and are described in, for example, Powels et al. (*Cloning Vectors: A Laboratory Manual,* Elsevier, N.Y., 1985). Such vectors may be readily adapted for use in the present invention. The expression vectors may comprise non-transcribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a poly-adenylation site, splice donor and acceptor sites, and transcriptional termination sequences.

Certain preferred mammalian expression vectors contain both prokaryotic sequences, to facilitate the propagation of the vector in bacteria (such as in an amplification step after recovery from the array), and one or more eukaryotic transcription units for expressing the target sequence in eukaryotic host cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors which can be readily adapted for use in the subject method. Some of these vectors are modified with sequences from bacterial plasmids, such as pBR322, to facilitate replication and drug resistance selection in both prokaryotic and eukaryotic cells. Alternatively, derivatives of viruses, such as the bovine papillomavirus (BPV-1), or Epstein-Barr virus (pHEBo, pREP-derived and p205) and the like, can be used to derive the subject arrays. The various methods employed in the preparation of the plasmids are well known in the art. For other suitable expression systems for both prokaryotic and eukaryotic cells, as well as general recombinant procedures, see *Molecular Cloning A Laboratory Manual,* 2nd Ed., ed. by Sambrook, Fritsch and Maniatis (Cold Spring Harbor Laboratory Press: 1989) Chapters 16 and 17.

Particularly preferred vectors contain regulatory elements that can be linked to the target sequence for transfection of mammalian cells, and include are cytomegalovirus (CMV) promoter-based vectors such as pcDNA1 (Invitrogen, San Diego, Calif.), MMTV promoter-based vectors such as pMAMNeo (Clontech, Palo Alto, Calif.) and pMSG (Pharmacia, Piscataway, N.J.), and SV40 promoter-based vectors such as pSVO (Clontech, Palo Alto, Calif.).

A number of vectors exist for the expression of recombinant proteins in yeast, where that is the host cell used in connection with the array. For instance, YEP24, YIP5, YEP51, YEP52, pYES2, and YRP17 are cloning and expression vehicles useful in the introduction of genetic constructs into *S. cerevisiae* (see, for example, Broach et al. (1983) in *Experimental Manipulation of Gene Expression,* ed. M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. Moreover, if yeast are used as a host cell, it will be understood that the expression of a gene in a yeast cell requires a promoter which is functional in yeast. Suitable promoters include the promoters for metallothionein, 3-phosphoglycerate kinase (Hitzeman et al., *J. Biol. Chem.* 255, 2073 (1980) or other glycolytic enzymes (Hess et al., *J. Adv. Enzyme Req.* 7, 149 (1968); and Holland et al. *Biochemistry* 17, 4900 (1978)), such as enolase, glyceraldehyde-3-phosphate dehydrogenase, hexokinase, pyruvate decarboxylase, phospho-fructokinase, glucose-6-phosphate isomerase, 3-phosphoglycerate mutase, pyruvate kinase, triosephosphate isomerase, phospho-glucose isomerase, and glucokinase.

In some instances, it may be desirable to derive the host cell using insect cells. In such embodiments, the transfection array can be derived from, for example, a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

Where the source of target sequence for the array are naturally occurring, those sequences can be isolated from any cell or collection of cells. For instance, the target sequences can be isolated from the cells of either adult tissue or organs or embryonic tissue or organs at any given developmental stage (including oocyte, blastocyte, etc.). The cells can be derived from healthy tissue or diseased tissue. In the case of a solid organ, the cell sample can be obtained by, e.g., biopsy. For blood, lymph and other bodily fluids, the cells can be isolated from the fluid component, e.g., by filtration, affinity purification, centrifugation or any other technique known in the art. The cells can be isolated to include a specific subset of phenotypes of cells from a given tissue, or can include be derived to include all or a substantial portion of cells representative of the tissue. For instance, the cells can be derived from an organ where the cells are particularly of epithelial, mesenchymal or endothelial origin. Subsets of cells can be isolated, for example, by use of cell surface markers or careful sectioning of a tissue.

In certain preferred embodiments, the target sequence are cDNA sequences derived from mRNA isolated from a cell or cells of interest. There are a variety of methods known in the art for isolating RNA from a cellular source, any of which may be used to practice the present method. The Chomczynski method, e.g., isolation of total cellular RNA by the guanidine isothiocyanate (described in U.S. Pat. No. 4,843,155) used in conjunction with, for example, oligo-dT strepavidin beads, is an exemplary mRNA isolation protocol. The RNA, as desirable, can be converted to cDNA by reverse transcriptase, e.g., poly(dT)-primered first strand cDNA synthesis by reverse transcriptase, followed by second strand synthesis (DNA pol I).

Likewise, there are a wide range of techniques for isolating genomic DNA which are amenable for use in a variety of embodiments of the subject method. In preferred embodiments, it will be desirable to isolate only a portion of the total genomic DNA on the basis of the chemical and/or physical state in which it is present in a collection of cells. For instance, transcriptionally active and/or potentially active genes can be distinguished by several criteria from inactive sequences. In higher eukaryoties, gene activation is accompanied by an increased general sensitivity to endonucleases like DNase I or micrococcal nuclease. This increased sensitivity probably reflects both the partial decondensation of chromatin. In addition, gene activation usually causes a coreplication domain that extends much beyond the decondensation domain. Chromatin digestion by DNase I, for example, will produce smaller digestion fragments from those areas of the genome which have undergone decondensation relative to areas of condensed chromatin structure (Galas et al. (1987) *Nucleic Acids Res.* 5:3157), e.g., the smaller fragments will be enriched for genomic sequences from genes in activated states.

Likewise, changes in methylation status of a gene provides another mechanism by which potential for expression can be altered, and may serve as a criteria for selecting certain genomic sequences as target nucleic acids. Thus, genomic DNA can be treated with methyl-sensitive restriction enzymes (such as DpnI) in order to produce endonuclease fragments of genes dependent on the methylation state of the surrounding genomic sequences.

In certain embodiments, the subject array can be made of a library of related, mutated sequences, such as a library of mutants of a particular protein, or libraries of potential promoter sequences, etc. There are a variety of forms of mutagenesis that can be utilized to generate a combinatorial library. For example, homologs of protein of interest (both agonist and antagonist forms) can be generated and isolated from a library by screening using, for example, alanine scanning mutagenesis and the like (Ruf et al. (1994) *Biochemistry* 33:1565–1572; Wang et al. (1994) *J. Biol. Chem.* 269:3095–3099; Balint et al. (1993) *Gene* 137:109–118; Grodberg et al. (1993) *Eur. J. Biochem.* 218:597–601; Nagashima et al. (1993) *J. Biol. Chem.* 268:2888–2892; Lowinan et al. (1991) *Biochemistry* 30:10832–10838; and Cunningham et al. (1989) *Science* 244:1081–1085), by linker scanning mutagenesis (Gustin et al. (1993) *Virology* 193:653–660; Brown et al. (1992) *Mol. Cell Biol.* 12:2644–2652; McKnight et al. (1982) *Science* 232:316); by saturation mutagenesis (Meyers et al. (1986) *Science* 232:613); by PCR mutagenesis (Leung et al. (1989) *Method Cell Mol Biol* 1:11–19); or by random mutagenesis (Miller et al. (1992) *A Short Course in Bacterial Genetics,* CSHL Press, Cold Spring Harbor, N.Y.; and Greener et al. (1994) *Strategies in Mol. Biol.* 7:32–34).

In another embodiment, the transfection array provides a library of small gene fragments as the target sequences, e.g., sequences which may encode dominant-acting synthetic genetic elements (SGEs), e.g., molecules that interfere with the function of genes from which they are derived (antagonists) or that are dominant constitutively active fragments (agonists) of such genes. SGEs that can be identified by the subject method include, but are not limited to, polypeptides, inhibitory antisense RNA molecules, ribozymes, nucleic acid decoys, and small peptides.

The SGEs identified by the present method may function to inhibit the function of an endogenous gene at the level of nucleic acids, e.g., by an antisense or decoy mechanism, or by encoding a polypeptide that is inhibitory through a mechanism of interference at the protein level, e.g., a dominant negative fragment of the native protein. On the other hand, certain SGEs may function to potentiate (including mimicking) the function of an endogenous gene by encoding a polypeptide which retains at least a portion of the bioactivity of the corresponding endogenous gene, and may in particular instances be constitutively active.

In one embodiment, the initial SGE library is generated from total cDNA, that may be further fragmented, and provided in the form of an expression library. Preferably, the inserts in the library will range from about 100 bp to about 700 bp and more preferably, from about 200 bp to about 500 bp in size.

For cDNA-derived libraries, the nucleic acid library can be a normalized library containing roughly equal numbers of clones corresponding to each gene expressed in the cell type from which it was made, without regard for the level of expression of any gene.

The initial SGE libraries can be generated to include both sense and antisense coding (and non-coding sequences) sequences. Transcription of the SGE sequence in the subtractive and target cells will create antisense RNA that may inhibit transcription of the corresponding endogenous gene. Translation of appropriate protein coding sequences in the transcribed RNA can produce full-length and truncated forms of endogenous proteins, as well as short peptides, the differential biological effects of that are assessed in the subtractive and target cells.

U.S. Pat. No. 5,702,898 describes a method to normalize a cDNA library constructed in a vector capable of being converted to single-stranded circles and capable of producing complementary nucleic acid molecules to the single-stranded circles comprising: (a) converting the cDNA library in single-stranded circles; (b) generating complementary nucleic acid molecules to the single-stranded circles; (c) hybridizing the single-stranded circles converted in step (a) with complementary nucleic acid molecules of step (b) to produce partial duplexes to an appropriate Cot; (e) separating the unhybridized single-stranded circles from the hybridized single-stranded circles, thereby generating a normalized cDNA library.

In certain embodiments, the SGE library can be a subtractive cDNA library. Many strategies have been used to create subtractive libraries, and can be readily adapted for use in the present method. One approach is based on the use of directionally cloned cDNA libraries as starting material (Palazzolo and Meyerowitz, (1987) *Gene* 52:197; Palazzolo et al. (1989) *Neuron* 3:527; Palazzolo et al. (1990) *Gene* 88:25). In this approach, cDNAs prepared from a first source tissue or cell line are directionally inserted immediately downstream of a bacteriophage T7 promoter in the vector. Total library DNA is prepared and transcribed in vitro with T7 RNA polymerase to produce large amounts of RNA that correspond to the original mRNA from the first source tissue. Sequences present in both the source tissue and another tissue or cells, such as normal tissue, are subtracted as follows. The in vitro transcribed RNA prepared from the first source is allowed to hybridize with cDNA prepared from either native mRNA or library RNA from the second source tissue. The complementarity of the cDNA to the RNA makes it possible to remove common sequences as they anneal to each other, allowing the subsequent isolation of unhybridized, presumably tissue-specific, cDNA. This approach is only possible using directional cDNA libraries, since any cDNA sequence in a non-directional library is as likely to be in the "sense" orientation as the "antisense" direction (sense and antisense are complementary to each other). A cDNA sequence unique to a tissue would be completely removed during the hybridization procedure if both sense and antisense copies were present.

In one directional cloning strategy, which can be used to generate an initial is SGE library, a DNA sequence encoding a specific restriction endonuclease recognition site (usually 6–10 bases) is provided at the 5' end of an oligo(dT) primer. This relatively short recognition sequence does not affect the annealing of the 12–20 base oligo(dT) primer to the mRNA, so the cDNA second strand synthesized from the first strand template includes the new recognition site added to the original 3' end of the coding sequence. After second strand cDNA synthesis, a blunt ended linker molecule containing a second restriction site (or a partially double stranded linker adapter containing a protruding end compatible with a second restriction site) is ligated to both ends of the cDNA. The site encoded by the linker is now on both ends of the cDNA molecule, but only the 3' end of the cDNA has the site introduced by the modified primer. Following the linker ligation step, the product is digested with both restriction enzymes (or, if a partially double stranded linker adapter was ligated onto the cDNA, with only the enzyme that recognizes the modified primer sequence). A population of cDNA molecules results which all have one defined sequence on their 5' end and a different defined sequence on their 3' end.

A related directional cloning strategy developed by Meissner et al. (1987) *PNAS* 84:4171), requires no sequence-specific modified primer. Meissner et al. describe a double stranded palindromic BamHI/HindIII directional linker having the sequence d(GCTTGGATCCAAGC) (SEQ ID NO: 1), that is ligated to a population of oligo(dT)-primed cDNAs, followed by digestion of the ligation products with BamHI and HindIII. This palindromic linker, when annealed to double stranded form, includes an internal BamHI site (GGATCC) (SEQ ID NO: 2) flanked by 4 of the 6 bases that define a HindIII site (AAGCTT) (SEQ ID NO: 3). The missing bases needed to complete a HindIII site are d(AA) on the 5' end or d(TT) on the 3' end. Regardless of the sequence to which this directional linker ligates, the internal BamHI site will be present. However, HindIII can only cut the linker if it ligates next to an d(AA):d(TT) dinucleotide base pair. In an oligo(dT)-primed strategy, a HindIII site is always generated at the 3' end of the cDNA after ligation to this directional linker. For cDNAs having the sequence d(TT) at their 5' ends (statistically 1 in 16 molecules), linker addition will also yield a HindIII site at the 5' end. However, because the 5' ends of cDNA are heterogeneous due to the lack of processivity of reverse transcriptases, cDNA products from every gene segment will be represented in the library.

In other embodiments, the SGE library is generated from genomic DNA fragments. Preferably, the inserts in the library will range from about 100 bp to about 700 bp and more preferably, from about 200 bp to about 500 bp in size. Such SGE libraries, in addition to encoding polypeptide and antisense molecules that may be functional SGEs in the test method, may also "encode" decoy molecules, e.g., nucleic acid sequences which correspond to regulatory elements of a gene and which can inhibit expression of the gene by sequestering, e.g., transcriptional factors, and thereby competing for the necessary components to express the endogenous gene.

In yet another embodiment, the SGE library is generated by randomly fragmenting a single gene to obtain a random fragment expression library derived exclusively from the gene of interest. As a practical matter, such a library will contain a much greater variety of SGEs derived from the gene of interest than will a random fragment library prepared from total cDNA. Consequently, the likelihood of obtaining optimized SGEs, that have a differential activity according to the present method, from the single gene random fragment library is much higher.

In one embodiment, purified DNA corresponding to the gene or genome to be suppressed is first randomly fragmented by enzymatic, chemical, or physical procedures. In a preferred embodiment, random fragments of DNA are produced by treating the DNA with a nuclease, such as DNase I. The random DNA fragments are incorporated as inserts in a SGE library. For general principles of DNase I partial digestion and library construction see *Molecular Cloning, A Laboratory Manual,* Sambrook et al., Eds., Cold Spring Harbor Laboratory, Cold Spring Harbor, N.Y.

In certain embodiments the inserted fragment may be expressed as part of a fusion protein. In other embodiments the inserted fragment alone may be expressed. In another embodiment, ribozyme-encoding sequences may be inserted directly adjacent to the insert to allow for selection of most efficient ribozyme-antisense clones. In still other embodiments the gene suppression element library may be further modified by random mutagenesis procedures known in the art. The inserted fragments may be expressed from either a constitutive or an inducible promoter.

In still another embodiment, the subject method is carried out with a library encoding a variegated population of small peptides, e.g., 4–25 amino acid residues in length. The library can be generated from coding sequences of total cDNA, or single genes, or can be random or semi-random in sequence. Small peptide fragments, corresponding to only a minute portion of a protein, can inhibit the function of that protein in vivo.

In still other embodiments, the subject method is carried out with a transfection array which, when the target sequence is transcribed in the host cell, gives rise to double stranded RNA, e.g., for use in identifying dsRNA constructs which produce a particular phenotype by RNA interference.

Libraries of coding sequences, whether encoding random peptides or full length proteins, may be expressed in many ways, including as portions of chimeric (fusion) proteins. In some instances it may be necessary to introduce an unstructured polypeptide linker region between portions of a chimeric protein derived from different proteins. This linker can facilitate enhanced flexibility of the chimeric protein allowing each portion to fold correctly and retain appropriate biological activity in the host cell. The linker can be of natural origin, such as a sequence determined to exist in random coil between two domains of a protein. Alternatively, the linker can be of synthetic origin. For instance, the sequence $(Gly_4Ser)_3$ can be used as a synthetic unstructured linker. Linkers of this type are described in Huston et al. (1988) PNAS 85:4879; and U.S. Pat. Nos. 5,091,513 and 5,258,498. Naturally occurring unstructured linkers of human origin are preferred as they reduce the risk of immunogenicity.

Where secretion of, e.g., a peptide library is desired, the peptide library can be engineered for secretion by including a secretion signal sequence as part of a fusion protein with the peptide.

In certain preferred embodiments, the transfection array provides, in a single array, e.g., preferably at least 10 different sequences, more preferably at least 100, 1000 or even 10,000 different, discrete sequences.

Preferably, target sequences are arrayed in an addressable fashion, such as rows and columns where the substrate is a planar surface.

If each feature size is about 100 microns on a side, each chip can have about 10,000 target sequence addresses (features) in a one centimeter square ($cm^2$) area. In certain preferred embodiments, the transfection array provides a density of at least $10^3$ different features per square centimeter ($10^3$ sequences/$cm^2$), and more preferably at least $10^4$ features/$cm^2$, $10^5$ features/$cm^2$, or even at least $10^6$ features/$cm^2$. Of course, lower densities are contemplated, such as at least 100 features/$cm^2$.

In certain embodiments, the transfection array provides multiple different target sequences in each feature, e.g., in order to promote co-transfection of the host cells with at least two different target sequences. Co-transfection refers to the simultaneous introduction of two or more plasmids or other DNA or nucleic acid constructs into the same cell. If the plasmids or nucleic acid constructs direct the expression of a gene product, such as a protein, RNA or other gene product, the cell will then express both gene products at the same time.

Co-transfections can be performed with transfected cell microarrays if the solution spotted on the surface where reverse transfection occurs contains more than one plasmid or nucleic acid construct. Of course, the collection of different target sequences in one feature should be distinct from other features of the array. The cotransfection features can include, for example, 2–10 different target sequences per feature, 10–100 different target sequences per feature, or even more than 100 different target sequences per feature.

The capacity to co-transfect cells in a transfected cell microarray has many important uses. These include but are not limited to the ability to: infer the expression of a gene product by detecting the expression of a co-transfected plasmid encoding a marker protein (e.g. GFP, luciferase, beta-galactosidase, or any protein to which a specific antibody is available), express all the components of a multi-subunit complex (e.g. the T-cell receptor) in the same cells, express all the components of a signal transduction pathway (e.g. MAP kinase pathway) in the same cells, and express all the components of a pathway that synthesizes a small molecule (e.g. polyketide synthetase). In addition, the capacity to co-transfect allows the creation of microarrays with combinatorial combinations of co-expressed plasmids. This capacity is particularly useful for implementing mammalian two-hybrid assays in which plasmids encoding bait and prey proteins are co-transfected into the same cells by spotting them in one feature of the microarray.

The capacity to co-transfect is also useful when the goal is to promote differentiation of the transfected cells along a certain tissue lineage. For example, combination of genes can be expressed in a stem or early progenitor cells that will force the differentiation of the cells into endothelial, liver, heart, pancreatic, lymphoid, islet, brain, lung, kidney or other cell types. In this fashion, arrays can be made with primary-like cells that can be used to examine interactions of protein or small molecules that are cell-type specific.

Furthermore, combinations of cDNAs can be printed in different patterns on the surface on which reverse transfection occurs. Patterns include, but are not limited to, bulls-eyes, squares, rectangles of varying heights and widths, and lines of single cell thickness. By printing, in particular patterns, combinations of cDNAs that cause differentiation of cells into different tissue types, this technology can be used to obtain arrays with distinct cell types in distinct locations. This capacity can be useful when trying to create tissue-like structures on the array, such as blood capillaries and stromal structures, or when studying the response of one cell type to the protein secretions of another cell type. For example, a secreting cell type can be created in the center of a bulls-eye pattern and responder cell types of different tissues can be created on the edge of bulls-eye. The response of the responder cells to the secretions of the center cell can then be examined.

Arrays containing mixtures of plasmids at each feature could be constructed, merely to illustrate, by mixing plasmids before printing, printing in serial, printing with masks, or printing with patterned printheads. For example, plasmids could be mixed in a container before printing and printed as a homogenous mixture. Alternatively, plasmids could be printed on top of one another or close to one another. In this method, the exact composition of the mixture containing each plasmid could be modified to control the sequencing and timing of their entry into a cell, e.g. slower or faster release mixtures. Masks with different patterns of holes or print heads with different configurations could also be used to print combinations of plasmids. For example, different enzymes involved in polyketide synthesis could be combined to generate different polyketides.

The carrier for use in the methods of the present invention can be, for example, gelatin or an equivalent thereof. In certain embodiments, the carrier is a hydrogel, such as polycarboxylic acid, cellulosic polymer, polyvinylpyrrolidone, maleic anhydride polymer, polyamide, polyvinyl alcohol, or polyethylene oxide.

Any suitable surface which can be used to affix the nucleic acid containing mixture to its surface can be used. For example, the surface can be glass, plastics (such as polytetrafluoroethylene, polyvinylidenedifluoride, polystyrene, polycarbonate, polypropylene), silicon, metal, (such as gold), membranes (such as nitrocellulose, methylcellulose, PTFE or cellulose), paper, biomaterials (such as protein, gelatin, agar), tissues (such as skin, endothelial tissue, bone, cartilage), minerals (such as hydroxylapatite, graphite). Additional compounds may be added to the base material of the surface to provide functionality. For example, scintillants can be added to a polystyrene substrate to allow Scintillation Proximity Assays to be performed. The substrate may be a porous solid support or non-porous solid support. The surface can have concave or convex regions, patterns of hydrophobic or hydrophilic regions, diffraction gratings, channels or other features. The scale of these features can range from the meter to the nanometer scale. For example, the scale can be on the micron scale for microfluidics channels or other MEMS features or on the nanometer scale for nanotubes or buckyballs. The surface can be planar, planar with raised or sunken features, spherical (e.g. optically encoded beads), fibers (e.g. fiber optic bundles), tubular (both interior or exterior), a 3-dimensional network (such as interlinking rods, tubes, spheres) or other shapes. The surface can be part of an integrated system. For instance, the surface can be the bottom of a microtitre dish, a culture dish, a culture chamber. Other components, such as lenses, gratings, and electrodes, can be integrated with the surface. In general, the material of the substrate and geometry of the array will be selected based on criteria that it be useful for automation of array formation, culturing and/or detection of cellular phenotype.

In still other embodiments, the solid support is a microsphere (bead), especially a FACS sortable bead. Preferably, each bead is an individual feature, e.g., having a homogenous population of target sequences and distinct from most other beads in the mixture, and one or more tags which can be used to the identify any given bead and therefore the target sequence it displays. The identity of any given target sequence that can induce a FACS-detectable change in cells that adhere to the beads can be readily determined from the tag(s) associate with the bead. For example, the tag can be an electrophoric tagging molecules that are used as a binary code (Ohlmeyer et al. (1993) *PNAS* 90:10922–10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (e.g., upwards of $10^{12}$) different molecules. A more versatile system has, however, been developed that permits encoding of essentially any combinatorial library. Here, the compound would be attached to the solid support via the photocleavable linker and the tag is attached through a catechol ether linker via carbene insertion into the bead matrix (Nestler et al. (1994) *J. Org. Chem.* 59:4723–4724). This orthogonal attachment strategy permits the FACS sorting of the cell/bead entities and subsequent decoding by ECGC after oxidative detachment of the tag sets from isolated beads. In other embodiments, the beads can be tagged with two or more fluorescently active molecules, and the identity of the bead is defined by the ratio of the various fluorophores.

In still another embodiment, the transfection array can be disposed on the end of a fiber optic system, such as a fiber optic bundle. Each fiber optic bundle contains thousands to millions of individual fibers depending on the diameter of the bundle. Changes in the phenotype of cells applied to the transfection array can be detected spectrometrically by conductance or transmittance of light over the spatially defined optic bundle. An optical fiber is a clad plastic or glass tube wherein the cladding is of a lower index of refraction than the core of the tube. When a plurality of such tubes are combined, a fiber optic bundle is produced. The choice of materials for the fiber optic will depend at least in part on the wavelengths at which the spectrometric analysis of the transfected cells is to be accomplished.

In addition, the surface can be coated with, for example, a cationic moiety. The cationic moiety can be any positively charged species capable of electrostatically binding to negatively charged polynucleotides. Preferred cationic moieties for use in the carrier are polycations, such as polylysine (e.g., poly-L-lysine), polyarginine, polyornithine, spermine, basic proteins such as histones (Chen et al. (1994) *FEBS Letters* 338:167–169), avidin, protamines (see e.g., Wagner et al. (1990) *PNAS* 87: 3410–3414), modified albumin (i.e., N-acylurea albumin) (see e.g., Huckett et al. (1990) *Chemi*- cal *Pharmacology* 40: 253–263), and polyamidoamine cascade polymers (see e.g., Haensler et al. (1993) *Bioconjugate Chem.* 4:372–379). A preferred polycation is polylysine (e.g., ranging from 3,800 to 60,000 daltons). Alternatively, the surface itself can be positively charged (such as gamma amino propyl silane or other alkyl silanes).

The surface can also be coated with molecules for additional functions. For instance, these molecules can be capture reagents such as antibodies, biotin, avidin, Ni-NTA to bind epitopes, avidin, biotinylted molecules, or 6-His tagged molecules. Alternatively, the molecules can be culture reagents such as extracellular matrix, fetal calf serum, collagen.

The present invention also encompasses methods of making arrays which comprise nucleic acid affixed to a surface such that when cells are plated onto the surface bearing the arrayed nucleic acid, the nucleic acid can be introduced (is introducible) into the cells (i.e., the nucleic acid can move from the surface into the cells). The present invention also encompasses a nucleic acid array comprising a surface having affixed thereto, in discrete, defined locations, nucleic acid of known sequence or source by a method described herein.

In certain embodiments, once the microarrays of transfected cells have formed (i.e., cDNAs in the spots have entered cells and the cells have expressed the encoded gene products), the microarrays can be transferred onto a variety of surfaces. Surfaces can be flexible or non-flexible and porous or non-porous. The surfaces can be flat or patterned with concave or convex regions, patterns of hydrophobic or hydrophilic regions, diffraction gratings, channels or other features. The scale of these features can range from the meter to the nanometer scale. Examples of surfaces include, but are not limited to, glass, plastics (such as polytetrafluoroethylene, polyvinylidenedifluoride, polystyrene, polycarbonate, polypropylene), silicon, metal, (such as gold), membranes (such as nitrocellulose, methylcellulose, PTFE or cellulose, polyvinylidene fluoride (PVDF)), paper, biomaterials (such as protein, gelatin, agar), tissues (such as skin, endothelial tissue, bone, cartilage), minerals (such as hydroxylapatite, graphite). Furthermore, many of these surfaces can be derivatized to provide additional functionalities. For example, scintillants can be added to a polystyrene substrate to allow Scintillation Proximity Assays to be performed. In another example, nitrocellulose membranes can be covalently modified with metal chelators that immobilize metals, such as nickel or cobalt, and allow the selective binding of proteins carrying a specific amino acid sequence, such as a hexa-histidine tag (6× His).

Transfers can be performed so that 1) the entire cellular material on the microarray is transferred (i.e. both the endogenous and recombinant materials made by the cells (RNA or protein)), or 2) so that only the recombinant material is transferred. The transfer of the microarray to another surface is accomplished by directly contacting the microarray to the other surface and allowing the material to move to the new surface under the influence of a force, such as capillary forces (commonly referred to as "blotting"), electric or magnetic fields, vacuum suction forces, or other forces. The material binds to the new surface through an interaction mediated by hydrophobic, hydrophillic, Van der Waals, ionic or other forces, or through specific receptor-ligand interactions (e.g. antibody-epitope interactions) or by becoming entangled in the molecular structure of the other surface.

The ability to transfer cellular material from the microarrays to another surface has many important uses. These include, but are not limited to, the capacity to detect cellular phenotypes or protein properties using techniques normally performed on specific surfaces and the capacity to in parallel purify the recombinant gene products expressed in the microarray. Examples of techniques normally performed on specific surfaces include western blotting, far-western blotting, southwestern blotting, surface plasmon resonance (SPR), mass spectroscopy, and others. These techniques normally require the immobilization of native or denatured proteins on nitrocellulose, nylon, paper, polyvinylidene fluoride (PVDF), or gold or other metal surfaces or membranes. Southwestern blotting is used to detect the interaction of a nucleic acid (such as DNA or RNA) with a protein. After transfer to an appropriate membrane, microarrays of cells expressing a collection of DNA binding proteins, such as transcription factors, could be used to identify binding proteins for genomic DNA sequence elements.

The transfer of microarrays to other surfaces is also useful for the in parallel purification of the recombinant proteins expressed on the microarray. In one embodiment of this approach, all the recombinant proteins expressed on the microarray contain an amino acid sequence that is a ligand for a specific protein or chemical reagent (e.g. an epitope recognized by a polyclonal or monoclonal antibody or a hexa-histidine tag recognized by a nickel affinity matrix). Microarrays expressing these proteins are then transferred by direct contact to a surface that has been derivatized with the reagent that binds the ligand (e.g. a nitrocellulose membrane to which an anti-epitope monoclonal antibody is bound or a nitrocellulose membrane derivatized with a metal chelator that allows the binding of nickel to its surface). After the material has bound to the new surface, the surface is washed with an appropriate buffer that does not disrupt the specific interaction but eliminates nonspecific interactions with the surface. Non-specific interactions include but are not limited to the interactions of any cellular components that do not contain the specific ligand recognized by the surface to which the microarray has been transferred. The microarray of recombinant proteins can then used to detect the interaction of other proteins or small molecules with the array. The binding of proteins or small molecules with the microarray can be detected with autoradiography, fluorescence, mass spectroscopy, immunofluorescence, or calorimetry.

Below is a proof of concept example for the transfer to a nitrocelluloes membrane of a microarray of cells expressing epitope-tagged proteins and growing on a glass slide.

Microarrays are transferred onto nitrocellulosemembranes and the proteins detected with standard western blotting protocols. The figure is an example of an array of myc-tagged proteins detected via enhanced chemiluminescence using a standard anti-myc western blotting protocol. The middle two rows (horizontally) are printed with half the amount of the expression construct as the top and bottom rows. The signal was detected with Kodak X-OMAT AR film and each spot is ~150 um in diameter.

To illustrate, when the microarrays are ready to be processed (usually 1–2 days after transfection), forceps are used to lift the slide from the culture dish and quickly rinse it with PBS (phosphate buffered saline) in a Coplin Jar. After the rinse, excess PBS is removed from the slide by briefly blotting its edge with an absorbent paper towel. The slide is then placed with the cells facing up on a flat surface, immobilized with tape and allowed to dry for 2–3 minutes (this time can vary depending on how much PBS remains on the slide). A nitrocellulose membrane about two to three times the area of the slide (0.45 $\mu$m pure nitrocellulose membrane; cat. 162-0116, BioRad) is then very carefully place on the slide, in a similar manner as is done for traditional plaque lifts (i.e. center first). At this time it is very important to not permit any horizontal movement of the membrane or slide at this step. The membrane is kept on the slide for 1–3 minutes or until the PBS has wetted the entire area of the membrane that covers the slide. It is important to not press down on or roll a pin over the membrane as this will invariably cause the membrane to slip and destroy the array. Also, it is important to not allow all the moisture on the slide to be transferred to the membrane as this will cause the membrane to stick to the slide and it will tear when it is lifted off. After transfer, the nitrocellulose membrane is carefully lifted off the slide surface with forceps and allowed it to air dry for 2 hours. After drying the membrane is dipped into a pH 11 CAPS-methanol transfer buffer (2.2 g/l CAPS, 10% methanol, pH 11) for 1–2 minutes and placed in a standard western blot blocking solution. The membrane is then processed with primary and secondary antibodies as in any standard western blotting protocol.

IV. Cells

Suitable host cells for generating the subject assay include prokaryotes, yeast, or higher eukaryotic cells, including plant and animal cells, especially mammalian cells. Prokaryotes include gram negative or gram positive organisms.

In certain preferred embodiments, the subject method is carried out using cells derived from higher eukaryotes, e.g., metazoans, and in especially preferred embodiments, are mammalian cells, and even more preferably are primate cells such as human cells. Other preferred species of mammalian cells include canine, feline, bovine, porcine, mouse and rat. For instance, such cells can be hematopoietic cells, neuronal cells, pancreatic cells, hepatic cells, chondrocytes, osteocytes, or myocytes. The cells can be fully differentiated cells or progenitor/stem cells.

Moreover, the cells can be derived from normal or diseased tissue, from differentiated or undifferentiated cells, from embryonic or adult tissue.

The cells may be dispersed in culture, or can be tissues samples containing multiple cells which retain some of the microarchitecture of the organ.

In certain embodiments, the transfection array of the subject invention is used to transfect a cell that can be co-cultured with a target cell. A biologically active protein secreted by the cells expressing genes from the transfection array will diffuse to neighboring target cells and induce a particular biological response, such as to illustrate, proliferation or differentiation, or activation of a signal transduction pathway which is directly detected by other phenotypic criteria. Likewise, antagonists of a given factor can be selected in similar fashion by the ability of the cell producing a functional antagonist to protect neighboring cells from the effect of exogenous factor added to the culture media. The host and target cells can be in direct contact, or separated by, e.g., a cell culture insert (e.g. Collaborative Biomedical Products, Catalog #40446).

If yeast cells are used, the yeast may be of any species which are cultivable and in the transfection array can be maintained upon transfection. Suitable species include *Kluyverei lactis, Schizosaccharomyces pombe*, and *Ustilaqo maydis; Saccharomyces cerevisiae* is preferred. Other yeast which can be used in practicing the present invention are *Neurospora crassa, Aspergillus niger, Aspergillus nidulans, Pichia pastoris, Candida tropicalis*, and *Hansenula polymorpha*. The term "yeast," as used herein, includes not only yeast in a strictly taxonomic sense, i.e., unicellular organisms, but also yeast-like multicellular fungi or filamentous fungi.

The choice of appropriate host cell will also be influenced by the choice of detection signal. For instance, reporter constructs can provide a selectable or screenable trait upon gain-of-function or loss-of-function induced by a target nucleic acid. The reporter gene may be an unmodified gene already in the host cell pathway, or it may be a heterologous gene (e.g., a "reporter gene construct"). In other embodiments, second messenger generation can be measured directly in a detection step, such as mobilization of intracellular calcium or phospholipid metabolism, in which case the host cell should have an appropriate starting phenotype for activation of such pathways.

The host cells are plated (placed) onto the surface bearing the transfection array in sufficient density and under appropriate conditions for introduction/entry of the nucleic acid into the cells. Preferably, the host cells (in an appropriate medium) are plated on the array at high density (e.g., on the order of $0.5-1\times10^5/cm^2$), in order to increase the likelihood that transfection will occur. For example, the density of cells can be from about $0.3\times10^5/cm^2$ to about $3\times10^5/cm^2$, and in specific embodiments, is from about $0.5\times10^5/cm^2$ to about $2\times10^5/cm^2$ and from about $0.5\times10^5/cm^2$ to about $1\times10^5/cm^2$. The appropriate conditions for introduction/entry of DNA into cells will vary depending on the quantity of cells used.

In certain embodiments, the host cells can engineered to express other recombinant genes. For instance, the host cells can be engineered with a reporter gene construct, and the ability of members of the transfection array to alter the level of expression of the reporter gene can be assessed. Merely to illustrate, the transfection array can be assessed for members which encode transcriptional activators or transcriptional repressors of the reporter gene, and may include native and non-native sequences. For instance, the host cell can be transfected with reporter gene construct including a promoter sequence for which a protein which binds that sequence is sought. The transfection array can encode a library of potential DNA binding domains fused to a polymerase activation domain. Members of the library are selected by their ability to induce expression of the reporter gene. Conversely, the DNA binding specificity of a DNA binding protein can be determined by arraying a library of reporter gene constructs which are variegated with respect to the sequence of a transcriptional regulatory element. The cell also expresses the DNA binding protein, e.g., which naturally or by engineering includes a transcriptional activation domain. Those members of the reporter gene construct library which include appropriate regulatory sequences are expressed, and the position of those constructs in the array used to determine the consensus sequence for the DNA binding protein.

In other instances, the host cells can be engineered so as to have a loss-of-function or gain-of-function phenotype, and the ability of the ability of members of the transfection array to counteract such a phenotype is assessed.

In still other instances, the host cells are engineered to express a recombinant cell surface receptor, and the transfection array encodes a variegated library of gene products or peptides, and the ability of one or more members of that library to induce or inhibit signal transduction by the receptor is assessed. For instance, the transfection array can provide a library of secreted peptides, and the ability of a given peptide to induce signal transduction is detected by the conversion of the cell to an autocrine phenotype.

V. Detection

A variety of methods can be used to detect the consequence of uptake, and in many embodiments, expression (at least transcription) of the target sequences. In a general sense, the assay provides the means for determining if the target sequence is able to confer a change in the phenotype of the cell relative to the same cell but which lacks the target sequence. Such changes can be detected on a gross cellular level, such as by changes in cell morphology (membrane ruffling, rate of mitosis, rate of cell death, mechanism of cell death, dye uptake, and the like). In other embodiments, the changes to the cell's phenotype, if any, are detected by more focused means, such as the detection of the level of a particular protein (such as a selectable or detectable marker), or level of mRNA or second messenger, to name but a few. Changes in the cell's phenotype can be determined by assaying reporter genes (beta-galactosidase, green fluorescent protein, beta-lactamase, luciferase, chloramphenicol acetyl transferase), assaying enzymes, using immunoassays, staining with dyes (e.g. DAPI, calcofluor), assaying electrical changes, characterizing changes in cell shape, examining changes in protein conformation, and counting cell number. Other changes of interest could be detected by methods such as chemical assays, light microscopy, scanning electron microscopy, transmission electron microscopy, atomic force microscopy, confocal microscopy, image reconstruction microscopy, scanners, autoradiography, light scattering, light absorbance, NMR, PET, patch clamping, calorimetry, mass spectrometry, surface plasmon resonance, time resolved fluorescence. Data could be collected at single or multiple time points and analyzed by the appropriate software.

For example, immunofluorescence can be used to detect a protein. Alternatively, expression of proteins that alter the phosphorylation state or subcellular localization of another protein, proteins that bind with other proteins or with nucleic acids or proteins with enzymatic activity can be detected.

In one embodiment, the screen can be for the inability to grow or survive when a parasite or infectious agent is added to the cell of interest. In this case the selection would be for knock-outs that are targeting genes that are specifically essential for some aspect of viral or parasitic function within a cell that are only essential when that cell is infected. Since some viral infection result in the induction of survival factors (such as CrmA, p35) it is likely that at least some cell functions are different and potentially selectively needed during viral, parasite growth.

Another type of screening method means is for the expression of a specific factor that can be measured and this measurement can be adapted for a screen. This factor can be anything that is accessible to measurement, including, but not limited to, secreted molecules, cell surface molecules, soluble and insoluble molecules, binding activities, activities that induce activities on other cells or induce other organic or inorganic chemical reactions. These interactions can be detected by Time Resolved Fluorescence, Surface Plasmon Resonance, Scintillation Proximity Assays, autoradiography, Fluorescence Activated Cell Sorting, or other methods.

Still another screening method is for changes in cell structure that are detected by any means that could be adapted for a selection scheme. This includes, but is not limited to, morphological changes that are measured by physical methods such as differential sedimentation, differential light scattering, differential buoyant density, differential cell volume selected by sieving, atomic force microscopy, and electron microscopy.

When screening for bioactivity of test compounds, intracellular second messenger generation can be measured directly. Such embodiments are useful where, for example, the arrayed library is being screened for target sequences which activate or inactivate a particular signaling pathway. A variety of intracellular effectors have been identified as being receptor- or ion channel-regulated, including adenylyl cyclase, cyclic GMP, phosphodiesterases, phosphoinositidases, phosphoinositol kinases, and phospholipases, as well as a variety of ions.

In one embodiment, the GTPase enzymatic activity by G proteins can be measured in plasma membrane preparations by determining the breakdown of $\gamma^{32}P$ GTP using techniques that are known in the art (For example, see *Signal Transduction: A Practical Approach,* G. Milligan, Ed., Oxford University Press, Oxford England). When receptors that modulate cAMP are tested, it will be possible to use standard techniques for cAMP detection, such as competitive assays which quantitate [$^3$H]cAMP in the presence of unlabelled cAMP.

Certain receptors and ion channels stimulate the activity of phospholipase C which stimulates the breakdown of phosphatidylinositol 4,5, bisphosphate to 1,4,5-IP3 (which mobilizes intracellular Ca++) and diacylglycerol (DAG) (which activates protein kinase C). Inositol lipids can be extracted and analyzed using standard lipid extraction techniques. DAG can also be measured using thin-layer chromatography. Water soluble derivatives of all three inositol lipids (IP 1, IP2, IP3) can also be quantitated using radiolabelling techniques or HPLC.

The other product of PIP2 breakdown, DAG can also be produced from phosphatidyl choline. The breakdown of this phospholipid in response to receptor-mediated signaling can also be measured using a variety of radiolabelling techniques.

The activation of phospholipase A2 can easily be quantitated using known techniques, including, for example, the generation of arachadonate in the cell.

In various cells, e.g., mammalian cells, specific proteases are induced or activated in each of several arms of divergent signaling pathways. These may be independently monitored by following their unique activities with substrates specific for each protease.

In the case of screening for ligands to certain receptors and ion channels, it may be desirable to screen for changes in cellular phosphorylation. Such assay formats may be useful when the host cell expresses a receptor of interest, such as a receptor kinase or phosphatase, and the arrayed library is being screened for peptide sequences which can act in an autocrine fashion, for example, immunoblotting (Lyons and Nelson (1984) *Proc. Natl. Acad. Sci. USA* 81:7426–7430) using anti-phosphotyrosine, anti-phosphoserine or abti-phosphothreonine antibodies. In addition, tests for phosphorylation could be also useful when the receptor itself may not be a kinase, but activates protein kinases or phosphatase that function downstream in the signal transduction pathway.

In yet another embodiment, the signal transduction pathway of the targeted receptor or ion channel upregulates expression or otherwise activates an enzyme which is capable of modifies a substrate which can be added to the cell. The signal can be detected by using a detectable substrate, in which case lose of the substrate signal is monitored, or alternatively, by using a substrate which produces a detectable product. In preferred embodiments, the conversion of the substrate to product by the activated enzyme produces a detectable change in optical characteristics of the test cell, e.g., the substrate and/or product is chromogenically or fluorogenically active. In an illustrative embodiment the signal transduction pathway causes a change in the activity of a proteolytic enzyme, altering the rate at which it cleaves a substrate peptide (or simply activates the enzyme towards the substrate). The peptide includes a fluorogenic donor radical, e.g., a fluorescence emitting radical, and an acceptor radical, e.g., an aromatic radical which absorbs the fluorescence energy of the fluorogenic donor radical when the acceptor radical and the fluorogenic donor radical are covalently held in close proximity (see, for example, U.S. Pat. Nos. 5,527,681, 5,506,115, 5,429,766, 5,424,186, and 5,316,691; and Capobianco et al. (1992) Anal. Biochem. 204:96–102. For example, the substrate peptide has a fluorescence donor group such as 1-aminobenzoic acid (anthranilic acid or ABZ) or aminomethylcoumarin (AMC) located at one position on the peptide and a fluorescence quencher group, such as lucifer yellow, methyl red or nitrobenzo-2-oxo-1,3-diazole (NBD), at a different position near the distal end of the peptide. A cleavage site for the activated enzyme will be diposed between each of the sites for the donor and acceptor groups. The intramolecular resonance energy transfer from the fluorescence donor molecule to the quencher will quench the fluorescence of the donor molecule when the two are sufficiently proximate in space, e.g., when the peptide is intact. Upon cleavage of the peptide, however, the quencher is separated from the donor group, leaving behind a fluorescent fragment. Thus, activation of the enzyme results in cleavage of the detection peptide, and dequenching of the fluorescent group.

In a preferred embodiment, the enzyme which cleaves the detection peptide is one which is endogenous to the host cell. For example, the bar1 gene of yeast encodes a protease, the expression of which is upregulated by stimulation of the yeast pheromone pathway. Thus, host cells which have been generated to exploit the pheromone signal pathway for detection can be contacted with a suitable detection peptide which can be cleaved by bar1 to release a fluorogenic fragment, and the level of bar1 activity thus determined.

In still other embodiments, the detectable signal can be produced by use of enzymes or chromogenic/fluorscent probes whose activities are dependent on the concentration of a second messenger, e.g., such as calcium, hydrolysis products of inositol phosphate, cAMP, etc. For example, the mobilization of intracellular calcium or the influx of calcium from outside the cell can be measured using standard techniques. The choice of the appropriate calcium indicator, fluorescent, bioluminescent, metallochromic, or Ca++-sensitive microelectrodes depends on the cell type and the magnitude and time constant of the event under study (Borle (1990) Environ. Health Perspect. 84:45–56). As an exemplary method of Ca++ detection, cells could be loaded with the Ca++ sensitive fluorescent dye fura-2 or indo-1, using standard methods, and any change in Ca++ measured using a fluorometer.

As certain embodiments described above suggest, the signal transduction activity for which an agonist or antagonist is sought in the arrayed library can be measured by detection of a transcription product, e.g., by detecting transcriptional activation (or repression) of an indicator gene(s). Detection of the transcription product includes detecting the gene transcript, detecting the product directly (e.g., by immunoassay) or detecting an activity of the protein (e.g., such as an enzymatic activity or chromogenic/fluorogenic activity); each of which is generally referred to herein as a means for detecting expression of the indicator gene. The indicator gene may be an unmodified endogenous gene of the host cell, a modified endogenous gene, or a part of a completely heterologous construct, e.g., as part of a reporter gene construct.

In one embodiment, the indicator gene is an unmodified endogenous gene. For example, the instant method can rely on detecting the transcriptional level of such endogenous genes as the c-fos gene (e.g., in mammalian cells) or the Bar1 or Fus1 genes (e.g., in yeast cells) in response to such signal transduction pathways as originating from G protein coupled receptors.

In certain instances, it may be desirable to increase the level of transcriptional activation of the endogenous indicator gene by the signal pathway in order to, for example, improve the signal-to-noise of the test system, or to adjust the level of response to a level suitable for a particular detection technique. In one embodiment, the transcriptional activation ability of the signal pathway can be amplified by the overexpression of one or more of the proteins involved in the intracellular signal cascade, particularly enzymes involved in the pathway. For example, increased expression of Jun kinases (JNKs) can potentiate the level of transcriptional activation by a signal in an MEKK/JNKK pathway. Likewise, overexpression of one or more signal transduction proteins in the yeast pheromone pathway can increase the level of Fus1 and/or Bar1 expression. This approach can, of course, also be used to potentiate the level of transcription of a heterologous reporter gene as well.

In other embodiments, the sensitivity of an endogenous indicator gene can be enhanced by manipulating the promoter sequence at the natural locus for the indicator gene. Such manipulation may range from point mutations to the endogenous regulatory elements to gross replacement of all or substantial portions of the regulatory elements. In general, manipulation of the genomic sequence for the indicator gene can be carried out using techniques known in the art, including homologous recombination.

In still another embodiment, a heterologous reporter gene construct can be used to provide the function of an indicator gene. Reporter gene constructs are prepared by operatively linking a reporter gene with at least one transcriptional regulatory element. If only one transcriptional regulatory element is included it must be a regulatable promoter. At least one the selected transcriptional regulatory elements must be indirectly or directly regulated by the activity of the selected cell-surface receptor whereby activity of the receptor can be monitored via transcription of the reporter genes.

Many reporter genes and transcriptional regulatory elements are known to those of skill in the art and others may be identified or synthesized by methods known to those of skill in the art.

Examples of reporter genes include, but are not limited to CAT (chloramphenicol acetyl transferase) (Alton and Vapnek (1979), Nature 282:864–869) luciferase, and other enzyme detection systems, such as beta-galactosidase; firefly luciferase (deWet et al. (1987), Mol. Cell. Biol. 7:725–737); bacterial luciferase (Engebrecht and Silverman (1984), PNAS 1:4154–4158; Baldwin et al. (1984), Biochemistry 23:3663–3667); alkaline phosphatase (Toh et al. (1989) Eur. J. Biochem. 182:231–238, Hall et al. (1983) J. Mol. Appl. Gen. 2:101), human placental secreted alkaline phosphatase (Cullen and Malim (1992) Methods in Enzymol. 216:362–368); β-lactamase, and GST.

Transcriptional control elements for use in the reporter gene constructs, or for modifying the genomic locus of an indicator gene include, but are not limited to, promoters, enhancers, and repressor and activator binding sites. Suitable transcriptional regulatory elements may be derived from the transcriptional regulatory regions of genes whose expression is linked to the desired phenotype sought from the arrayed library.

In the case of receptors which modulate cyclic AMP, a transcriptional based readout can be constructed using the cyclic AMP response element binding protein, CREB, which is a transcription factor whose activity is regulated by phosphorylation at a particular serine (S133). When this serine residue is phosphorylated, CREB binds to a recognition sequence known as a CRE (cAMP Responsive Element) found to the 5' of promoters known to be responsive to elevated cAMP levels. Upon binding of phosphorylated CREB to a CRE, transcription from this promoter is increased.

Phosphorylation of CREB is seen in response to both increased cAMP levels and increased intracellular Ca levels. Increased cAMP levels result in activation of PKA, which in turn phosphorylates CREB and leads to binding to CRE and transcriptional activation. Increased intracellular calcium levels results in activation of calcium/calmodulin responsive kinase II (CaM kinase II). Phosphorylation of CREB by CaM kinase II is effectively the same as phosphorylation of CREB by PKA, and results in transcriptional activation of CRE containing promoters.

Therefore, a transcriptionally-based readout can be constructed in cells containing a reporter gene whose expression is driven by a basal promoter containing one or more CRE. Changes in the intracellular concentration of Ca++ (a result of alterations in the activity of the receptor upon engagement with a ligand) will result in changes in the level of expression of the reporter gene if: a) CREB is also co-expressed in the cell, and b) either an endogenous or heterologous CaM kinase phosphorylates CREB in response to increases in calcium or if an exogenously expressed CaM kinase II is present in the same cell. In other words, stimulation of PLC activity may result in phosphorylation of CREB and increased transcription from the CRE-construct, while inhibition of PLC activity may result in decreased transcription from the CRE-responsive construct.

In preferred embodiments, the reporter gene is a gene whose expression causes a phenotypic change which is screenable or selectable. If the change is selectable, the phenotypic change creates a difference in the growth or survival rate between cells which express the reporter gene and those which do not. If the change is screenable, the phenotype change creates a difference in some detectable characteristic of the cells, by which the cells which express the marker may be distinguished from those which do not. Selection is preferable to screening in that it can provide a means for amplifying from the cell culture those cells which express a test polypeptide which is a receptor effector.

The marker gene is coupled to the receptor signaling pathway so that expression of the marker gene is dependent on activation of the receptor. This coupling may be achieved by operably linking the marker gene to a receptor-responsive promoter. The term "receptor-responsive promoter" indicates a promoter which is regulated by some product of the target receptor's signal transduction pathway.

Alternatively, the promoter may be one which is repressed by the receptor pathway, thereby preventing expression of a product which is deleterious to the cell. With a receptor repressed promoter, one screens for agonists by linking the promoter to a deleterious gene, and for antagonists, by linking it to a beneficial gene. Repression may be achieved by operably linking a receptor-induced promoter to a gene encoding mRNA which is antisense to at least a portion of the mRNA encoded by the marker gene (whether in the coding or flanking regions), so as to inhibit translation of that mRNA. Repression may also be obtained by linking a receptor-induced promoter to a gene encoding a DNA binding repressor protein, and incorporating a suitable operator site into the promoter or other suitable region of the marker gene.

In the case of yeast, suitable positively selectable (beneficial) genes include the following: URA3, LYS2, HIS3, LEU2, TRP1; ADE1,2,3,4,5,7,8; ARG1,3,4,5,6,8; HIS1,4,5; ILV1,2,5; THR1,4; TRP2,3,4,5; LEU1,4; MET2, 3,4,8,9,14,16,19; URA1,2,4,5,10; HOM3,6; ASP3; CHO1; ARO 2,7; CYS3; OLE1; IN01, 2,4; PR01,3 Countless other genes are potential selective markers. The above are involved in well-characterized biosynthetic pathways. The imidazoleglycerol phosphate dehydratase (IGP dehydratase) gene (HIS3) is preferred because it is both quite sensitive and can be selected over a broad range of expression levels. In the simplest case, the cell is auxotrophic for histidine (requires histidine for growth) in the absence of activation. Activation leads to synthesis of the enzyme and the cell becomes prototrophic for histidine (does not require histidine). Thus the selection is for growth in the absence of histidine. Since only a few molecules per cell of IGP dehydratase are required for histidine prototrophy, the assay is very sensitive.

The marker gene may also be a screenable gene. The screened characteristic may be a change in cell morphology, metabolism or other screenable features. Suitable markers include beta-galactosidase (Xgal), $C_{12}FDG$, SALMON-gal (6-Chloro-3-indoxyl-beta-D-galactopyranoside), MAGENTA-Gal (5-Bromo-6-chloro-3-indoxyl-beta-D-galactopyranoside) (latter two from Biosynth Ag), alkaline phosphatase, horseradish peroxidase, exo-glucanase (product of yeast exb1 gene; nonessential, secreted), luciferase, bacterial green fluorescent protein, (human placental) secreted alkaline phosphatase (SEAP), and chloramphenicol transferase (CAT). Some of the above can be engineered so that they are secreted (although not β-galactosidase). A preferred screenable marker gene is beta-galactosidase; yeast cells expressing the enzyme convert the colorless substrate Xgal into a blue pigment. Again, the promoter may be receptor-induced or receptor-inhibited.

VI. Exemplary Uses

A. Target Identification

The binding partners for molecules such as drugs, hormones, interleukins, or secreted proteins can be identified by incubating the compounds of interest with an array that overexpresses potential targets within each array feature or combinations of potential targets within each cell of an array feature. Binding could be detected by methods such as SPR, SPA, TRF, or autoradiography. In addition, the binding partners for cells could be identified by incubating the cell of interest with arrays or color-encoded beads. For instance, migratory or free-floating test cells could be incubated with an array, allowed to migrate or bind, and then the binding or migration detected by standard methods, e.g. expressing GFP or other markers in the test cells. Alternatively, the test cells could be mixed with a collection of color-encoded beads, each expressing a distinct DNA construct with a unique color code, e.g. a unique ratio of red to green dyes. Binding could then be detected by fluorescence activated cell sorting or other methods.

The array could also be used to identify the targets of an organism's immune response to cancer, an infectious or autoimmune disease, exposure to chemicals, or environmental changes. An array expressing target proteins could be incubated with sera from the organism. Binding of antibodies could be detected by labeling the sera or using the appropriate secondary antibody. The identified targets of the immune response could be used to design vaccines against tumors or infectious diseases, immunosuppressive drugs, anti-infective drugs or others.

In other embodiments, the present invention facilitates drug target discovery by permitting the identification of an endogenous gene whose inhibit or activation may be of therapeutic value. The strategy relies, in part, on the ability of small gene fragments to encode dominant-acting synthetic genetic elements (SGEs), e.g., molecules that interfere with the function of genes from which they are derived (antagonists) or that are dominant constitutively active fragments (agonists) of such genes. SGEs that can be identified by the subject method include, but are not limited to, polypeptides, inhibitory antisense RNA molecules, ribozymes, nucleic acid decoys, and small peptides. For instance, a gene whose activity is inactivated by an identified SGE can itself be used as a target for drug development, e.g., to identify other agents, such as small molecules and natural extracts, which can also inhibit the function of the endogenous gene. Thus, another aspect of the present invention, provides drug screening assays for detecting agonists or antagonists, as appropriate, of a gene (or gene product thereof) that corresponds to a selected SGE. Likewise, the identification of an SGE that can inhibit a particular pathological phenotype will indicate diagnostic assays that can assess loss-of-function or gain-of-function mutations, as appropriate, to the corresponding endogenous gene.

In other embodiments, the use of transcription arrays which give rise to dsRNA in the host cell can be used to assess the loss-of-function of a particular gene. "RNA interference," "post-transcriptional gene silencing," "quelling"—these different names describe similar effects that result from the overexpression or misexpression of transgenes, or from the deliberate introduction of double-stranded RNA into cells (reviewed in Fire A (1999) *Trends Genet.* 15:358–363; Sharp P A (1999) *Genes Dev* 13:139–141; Hunter C. (1999) *Curr. Biol.* 9:R440–R442; Baulcombe D. C. (1999) *Curr. Biol.* 9:R599–R601; Vaucheret et al. (1998) *Plant J.* 16:651–659). The injection of double-stranded RNA into a cell can act systemically to cause the post-transcriptional depletion of the homologous endogenous RNA (Fire et al. (1998) *Nature* 391:806–811; and Montgomery et al. (1998) *PNAS* 95:15502–15507). RNA interference, commonly referred to as RNAi, offers a way of specifically and potently inactivating a cloned gene, and is proving a powerful tool for investigating gene function.

To illustrate, the subject method contemplates (a) constructing a cDNA or genomic transfection array including cDNA or genomic DNA in an orientation relative to a promoter(s) capable of initiating transcription of the cDNA or genomic DNA to double stranded RNA; (b) introducing the transfection array into cells by the subject method; (c) identifying and isolating cells in which a member of the transfection array confers a particular phenotype; and (d) identifying the gene sequence from the library which gave rise to the dsRNA construct responsible for conferring the phenotype.

B. Target Validation

The expression pattern of potential genes of interest could be tested by constructing an array where each spot contains a construct fusing regulatory sequences from the genes of interest with a reporter gene. The regulatory sequences could be involved in transcription, RNA processing or translation. The reporter gene could be GFP, beta galactosidase, luciferase, beta lactamase or other genes. The expression of the genes of interest could be tested by incubating the array with different combinations of conditions and cell lines and then assaying for the activity of the reporter gene. Genes with the appropriate expression patterns could then be studied further as potential drug targets.

The function of the gene of interest could be tested by making arrays where DNA constructs modify the function of the gene of interest and assaying the phenotype. These modifications could be derived from methods such as overexpression, knockout constructs, dominant negative mutants, anti-sense RNA, ribozyme RNA or others. The resulting phenotypic change could be assayed under different environmental conditions, genetic backgrounds and cell types. For instance, genes which activate or inhibit a pathway could be identified by examining the phenotype of cells on an array where each feature overexpresses or underexpresses a gene of interest. Genes with the appropriate phenotypes could then be studied further as potential drug targets.

The function of a gene of interest could also be inferred by identifying the binding partners for a protein of interest. For instance, an array expressing proteins of interest could be tested for DNA binding, RNA binding, protein binding, nucleotide binding or other functions by incubating the array with the appropriately labeled molecule and/or detection system. Different classes of proteins, e.g., DNA-binding proteins, could be identified and the sequences examined for the discovery of novel binding motifs. Alternatively, a two hybrid or three hybrid system could be used to identify potential protein, RNA, or other classes of binding partners in vivo. For instance, the gene of interest could be cloned into the appropriate "bait" vector and stably transfected in a cell line with the appropriate reporter construct. The interaction of the gene of interest with other potential partners could be tested by using this cell line in an array of constructs where test proteins are cloned into the appropriate "test" vector. Alternatively, an array of affinity tagged constructs (e.g., 6× His, epitopes, avidin) could be transferred to an affinity membrane, e.g., (Ni-NTA, anti-epitope antibody, biotinylated). Associated proteins could be detected and identified by mass spec or other methods. Proteins with the appropriate binding partners could then be further investigated as potential targets.

The function of a gene of interest could also be inferred by identifying its post-translational modifications. An array expressing proteins of interest could be tested for phosphorylation, sulfation, ubiquitination, glycosylation or other post-translational modifications by incubation with the appropriate labeling or detection reagent such as radiolabeled precursors, anti-phosphoamino acid antibodies, anti-ubiquitin, lectins or other specific detection reagents. Alternatively, post-translational modifications could be detected by transferring the array to an affinity membrane and then using mass spectrometry.

Subcellular localization of a protein could be investigated by making an array where each feature contains a DNA construct with the protein of interest fused to an epitope tag, GFP or other marker. After transfection and cell growth, immunofluorescence could be performed with a microscope, high resolution scanner or other detection method to determine whether the proteins of interest localized to the nucleus, cytoplasm, membrane, extracellular or other compartments. Proteins with the appropriate subcellular localization could then be further investigated as potential targets.

C. Screening

Large molecule therapeutics (such as proteins, nucleic acids, sugars) could be identified by making an array of the appropriate constructs and screening for the desired phenotype. For instance, a screen for secreted proteins could involve an array where cells expressing secreted proteins are mixed with tester cells with the potential for an assayable response to the secreted proteins. After transfection and growth, the response of the tester cells could be measured to identify features producing secreted proteins with the desired effect.

Multiplexed screening could be performed by making arrays on the bottom of each well of a microtiter dish. The binding of molecules to an array of 100 or more potential targets in the bottom of each well. These targets could be pharmacogenomic variants, families of proteins, or other collections of proteins. The binding could then be assayed by a scanner, plate reader or other instrument, (e.g., Cellomics ARRAYSCAN II).

Arrays could also be used to characterize compound libraries. Binding of compound mixtures to targets in the array could be characterized to provide an overall assessment the diversity of the mixture. High diversity mixtures would bind to more targets than low diversity mixtures. The mixture could be, for example, a combinatorial library or natural product extract.

D. Lead Optimization

Potential drug candidates could be evaluated for selectivity by incubating the candidate with the appropriate array of potential targets. The arrays could be the entire set of genes in the genome(s) of interest or focused subsets, e.g. GPCRs, ion channels, enzymes, nuclear hormone receptors. The relative binding of the drug candidate to the known target and other potential targets could be determined. Candidates with a high degree of non-selective binding could be abandoned or modified to reduce non-selective binding before additional testing such as ADME ortoxicology other tests. Potential drug candidates could be evaluated for toxicity by incubating the candidate with the appropriate array of targets, such as cytochrome P-450s, including pharmacogenomic variants or other variations.

Selectivity tests could also be performed on the metabolites of a drug candidate. For instance, a radiolabeled drug could be reacted with the appropriate biotransformation agent, such as a liver extract, tissue culture system, or living organism such as a rodent or dog. The radiolabeled metabolites could then be extracted and purified and tested for binding with the array. Metabolites with binding activity could then be characterized further by standard methods. Two embodiments of the present method are described in detail herein: a DNA-gelatin method, in which a mixture comprising DNA (e.g., DNA in an expression vector, such as, a plasmid-based or viral-based vector) and a carrier protein (e.g., gelatin) is used and a lipid vector-DNA method, in which a mixture comprising DNA, such as DNA in an expression vector (e.g., a plasmid); a carrier protein (e.g., gelatin); a sugar (e.g., sucrose); DNA condensation buffer; and an appropriate lipid-containing transfection reagent is used. Any suitable gelatin which is non-toxic, hydrated, which can immobilize the nucleic acid mixture onto a surface and which also allows the nucleic acid immobilized on the surface to be introduced over time into cells plated on the surface can be used. For example, the gelatin can be a crude protein gelatin or a more pure protein based gelatin such as fibronectin. In addition, a hydrogel, a sugar based gelatin (polyethylene glycol) or a synthetic or chemical based gelatin such as acrylamide can be used.

In the first embodiment, a mixture comprising two components (DNA such as DNA in an expression vector and a carrier protein) is spotted onto a surface (e.g., a slide) in discrete, defined locations or areas and allowed to dry. One example of this embodiment is described in Example 1.

After the carrier (e.g., gelatin)-DNA mixture has dried sufficiently that it is affixed to the surface, transfection reagents (a lipofection mixture) and cells to be reverse transfected are added, preferably sequentially. The transfection mixture can be one made from available components or can be a commercially available lipofection mixture, such as EFFECTENE™ (Qiagen), FUGENE 6™ (Boehringer Mannheim) or LIPOFECTAMINE™ (Gibco/BRL-Life Technologies). It is added in an appropriate quantity, which can be determined empirically, taking into consideration the amount of DNA in each defined location. A wax barrier can be drawn around the locations on the surface which contain the vector-DNA mixture, prior to addition of the transfection mixture, in order to retain the mixture or the solution can be kept in place using a cover well. Generally, in this embodiment, the transfection reagent is removed, such as by vacuum suctioning, prior to addition of cells into which DNA is to be reverse transfected. Actively growing cells are plated on top of the locations, producing a surface that bears the DNA-containing mixture in defined locations. The resulting product is maintained under conditions (e.g., temperature and time) which result in entry of DNA in the DNA spots into the growing cells. These conditions will vary according to the types of cells and reagents used and can be determined empirically. Temperature can be, for example, room temperature or 37° C., 25° C., or any temperature determined to be appropriate for the cells and reagents.

In the second embodiment, one example of which is described in Example 2, a mixture comprising DNA in an expression vector; a carrier protein (e.g., gelatin); a sugar (e.g., sucrose); DNA condensation buffer; and a lipid-based transfection reagent is spotted onto a surface, such as a slide, in discrete, defined locations and allowed to dry. Actively growing cells are plated on top of the DNA-containing locations and the resulting surface is maintained under conditions (e.g., temperature and time) which result in entry of DNA in the DNA spots into the growing cells (reverse transfection). Expression of DNA in cells is detected using known methods, as described above.

E. Optimization of Plasmids

In still another embodiment, the subject method can be used to optimize an expression system for a particular cell type. Briefly, the transfection array can be a collection of various permutations of a vector system. For instance, the vector library can test various combinations and permutations of promoter and enhance sequences, replication origins, and other components which could effect the level of expression of a protein or the stability of the cell line for the plasmid.

VII. Exemplary Embodiments

The present invention is illustrated by the following examples, which are not intended to be limiting in any way.

EXAMPLE 1

Reverse Transfection: "Gelatin-DNA" Method

Materials

[DNA]: 1 $\mu g/\mu L$ (e.g., HA-GST pRK5, pBABE CMV GFP)

Gelatin (ICN, cat. #901771): 0.2% stock in ddH$_2$O, all dilutions made in PBS-0.20% gelatin=0.5 g gelatin+250 mL ddH$_2$O EFFECTENE™ Transfection Kit (Qiagen, cat. #301425)

Plasmid-DNA: grown in 100 mL L-amp overnight from glycerol stock, purified by standard QIAPREP Miniprep or Qiagen Plasmid Purification Maxi protocols Cell Type: HEK 293T cultured in DMEM/10%IFS with L-glut and pen/strep Diluting and Spotting DNA Dilute DNA in 0.2% gelatin* to give final [DNA]=0.05 µg/µL**

* range of gelatin concentration that worked under the conditions used=0.05% to 0.5%
 range of DNA concentrations that worked under the conditions used 0.01 µg/µl to 0.10 µg/µl Spot DNA/gelatin mix on Σ poly-L-lysine slides using arrayer Allow slides to dry in vacuum-dessicator overnight*

*** range of drying time=2 hours to 1 week

Adding Tx. Reagents to Gelatin-DNA Spots

In eppendorf tube, mix 300 µL DNA-condensation buffer (EC Buffer)+16 µL Enhancer Mix by vortexing. Incubate for 5 minutes Add 50 µL EFFECTENE™ and mix by pipetting Draw a wax circular barrier on slide around spots to apply the transfection reagent Add 366 µL mix to wax-enclosed region of spots Incubate at room temperature for 10 to 20 minutes Meanwhile, split cells to reverse-transfect Vacuum-suction off reagent in hood Place slides in dish and add cells for reverse transfection Splitting Cells Split actively growing cells to [cell]=$10^7$ cells in 25 mL Plate cells on top of slide(s) in square 100×100×15 mm petri dish Allow reverse transfection to proceed for 40 hours= approx. 2 cell cycles Process slides for immunofluorescence

EXAMPLE 2

Reverse Transfection: "Lipid-DNA" Method

Materials

[DNA]: 1 µg/µL (e.g., HA-GST pRK5, pBABE CMV GFP)

Gelatin (ICN, cat.#901771): 0.2% stock in ddH$_2$O, all dilutions made in PBS$^-$ 0.05% gelatin=250 µL 0.2%+750 µL PBS$^-$ EFFECTENE™ Transfection Kit (Qiagen, cat.#301425):

EC Buffer in 0.4M sucrose=273.6 µL 50% sucrose+726.4 µL EC Buffer

Plasmid-DNA: grown in 100 mL L-amp overnight from glycerol stock, purified by standard QIAPREP™ Mini-prep or Qiagen Plasmid Purification Maxi protocols Cell Type: HEK 293T cultured in DMEM/10%IFS with L-glut and pen/strep Reverse Transfection Protocol with Reduced Volume Aliquot 1.6 µg DNA in separate eppendorf tubes Add 15 µL of pre-made DNA-condensation buffer (EC Buffer) with 0.4M sucrose* to tubes

* range of sucrose that worked under the conditions used=0.1M to 0.4M

Add 1.6 µL of Enhancer solution and mix by pipetting several times. Incubate at room temperature for 5 minutes Add 5 µL of EFFECTENE™ Transfection Reagent to the DNA-Enhancer mix and mix by pipetting. Incubate at room temperature for 10 minutes Add 23.2 µL of 0.05% gelatin** to total transfection reagent mix (i.e. 1:1 dilution)

** range of gelatin concentration that worked under the conditions used= 0.01% to 0.05%

Spot lipid-DNA on Σ poly-L-lysine slides mix using arrayer

Allow slides to dry in vacuum-dessicator overnight***

EFFECTENE™ kit (Qiagen) used includes Enhancer solution, which was used according to Qiagen's instructions.

*** range of drying time=2 hours to 1 week

Splitting Cells

Split actively growing cells to [cell]=$10^7$ cells in 25 mL

Plate cells on top of slide(s) in square 100×100×15 mm petri dish

Allow reverse transfection to proceed for 40 hours= approx. 2 cell cycles

Process slides for immunofluorescence

EXAMPLE 3

Transfected Cells Microarrays: A Genomics Approach for the Analysis of Gene Products in Mammalian Cells Lipid-DNA Method I. Gelatin Preparation and DNA Purification Materials:

Gamma-Amino Propyl Silane (GAPS) slides (Corning catalog #2550),

Purified cDNA,

Gelatin, Type B: 225 Bloom (Sigma, catalog #G-9391),

Methods 0.2% Gelatin was made by incubation in a 60° C. water bath for 15 minutes. The gelatin was cooled slowly to 37° C. at which point it was filtered through 0.45 µm cellular acetate membrane (CA).

Bacterial clones with DNA plasmids were grown in a 96 Deep-Well Dish for 18 to 24 hours in 1.3 mL of terrific broth (TB) shaking at 250 rpm at 37° C. The plasmids were miniprepped and optical density (OD) was taken. DNA purity, as indicated by final 280 nm/260 nm absorbance ratio, was greater than 1.7.

Storage

For storage purposes, gelatin was kept at 4° C. and miniprepped DNA kept at −20° C.

II. Sample Preparation and Array Printing

Materials

EFFECTENE™ Transfection Reagent (Qiagen catalog #301425),

Sucrose (Life Technologies),

INTEGRID™ 100 mm ×15 mm Tissue Culture Square Petri Dishes (Becton Dickinson: Falcon catalog #35-1012), Costar 384-well plates (VWR catalog #7402), STEALTH MICRO SPOTTING PINS, (Telechem International, Inc. catalog #SMP4), PIXSYS 5500 Robotic Arrayer (Cartesian Technologies, Model AD20A5), Vacuum Dessicator with Stopcock 250 mm, NALGENE™ (VWR catalog #24987-004), DRIERITE™ Anhydrous Calcium Sulfate (VWR catalog #22890-229)

Forceps to hold slides,

Human Embryonic Kidney (HEK) 293T cells,

Tissue Culture hood,

Cover Slips (50 mm ×25 mm),

Methods

For each DNA-containing spot, 15 µl of pre-made DNA-condensation buffer (Buffer EC) with 0.2M to 0.4M sucrose was added to 0.80 µg to 1.60 µg DNA in a separate eppendorf tube. Subsequently, 1.5 µl of the Enhancer solution was added to the tube and mixed by pipetting. This was let to incubate at room temperature for 5 minutes. 5 µl EFFECTENE transfection reagent was added, mixed and let to incubate at room temperature for 10 minutes with the DNA-Enhancer mixture. 1× volume of 0.05% gelatin was added, mixed and the appropriate amount was aliquoted into a 384-well plate for arraying purposes.

The PIXSYS™ 5500 Robotic Arrayer was used with Telechem's ARRAYIT™ STEALTH PINS (SMP4) with each spot spaced 400 μm apart with a 50 ms to 500 ms delay time of the pin on the slide for each spot. A 55% relative humidity environment was maintained during the arraying. A thorough wash step was implemented between each dip into a DNA sample in the 384-well plate to avoid clogging of the pins that would result in missing spots in the array.

In a tissue culture hood, $10 \times 10^6$ Human Embryonic Kidney (HEK) 293T cells were prepared in 25 ml DME media with 10% IFS, pen/strep and glutamine for every 3 slides that were to be processed. After arraying, the slides were simply placed array-side facing up on a sterile 100× 100×10 mm square dish (3 slides per plate) and the cells were poured gently on the slides while avoiding direct pouring on the arrays themselves. If the number of slides were not a multiple of 3, dummy slides were placed to cover the square dish.

The cells were let to grow on the arrays for approximately 2 cell cycles (~40 hours for 293T). Subsequently, the slides were very gently rinsed with PBS⁻ in a Coplin jar, and then fixed in 3.7% paraformaldehyde/4.0% sucrose for 20 minutes in a Coplin jar, and then transferred back to ajar with PBS⁻.

Storage

After arraying, slides were stored at room temperature in a vacuum dessicator with anhydrous calcium sulfate pellets. After fixation, slides were kept in PBS⁻ at 4° C. until analyses were completed (maximum of 5 days).

III. Methods of Detection

Immunofluorescence

Fluorescence Microscopy

Laser Scanning

Radiolabelling and detection with sensitive film or emulsion

If the expressed proteins to be visualized are fluorescent proteins, they can be viewed and photographed by fluorescent microscopy. For large expression array, slides may be scanned with a laser scanner for data storage. If a fluorescent antibody can detect the expressed proteins, the protocol for immunofluorescence can be followed. If the detection is based on radioactivity, the slides can be fixed as indicated above and radioactivity detected by autoradiography with film or emulsion.

Immunofluorescence

After fixation, the array area was permeabilized in 0.1% TRITON X-100 in PBS⁻ for 15 minutes. After two rinses in PBS⁻, the slides were blocked for 60 minutes, probed with a primary antibody at 1:200 to 1:500 dilution for 60 minutes, blocked for 20 minutes, probed with a fluorescent secondary antibody at 1:200 dilution for 40 minutes. The slides can be transferred to a Coplin jar in PBS⁻and visualized under an upright fluorescent microscope. After analyses, the slides can be mounted and stored in the dark at 4° C.

To create these microarrays, distinct and defined areas of a lawn of cells were simultaneously transfected with different plasmid DNAs (FIG. 4A). This is accomplished without the use of individual wells to sequester the DNAs. Nanoliter volumes of plasmid DNA in an aqueous gelatin solution are printed on a glass slide. A robotic arrayer (PIXSYS™ 5500, Cartesian Technologies) equipped with STEALTH PINS (SMP4, Telechem) was used to print a plasmid DNA/gelatin solution contained in a 384-well plate onto CMT GAPS glass slides (Corning). The pins deposited ~1 nl volumes 400 μm apart using a 25 ms pin down slide time in a 55% relative humidity environment. Printed slides were stored at room temperature in a vacuum desiccator until use. Preparation of aqueous gelatin solution is important and is as follows, 0.02% gelatin (w/v) (Sigma G-9391) was dissolved in MILLIQ™ water by heating and gentle swirling in a 60° C. water bath for 15 minutes. The solution was cooled slowly to room temperature and filtered through a 0.45 μm cellular acetate membrane and stored at 4° C. Plasmid DNA was purified with the Plasmid Maxi or QIAPREP™ 96 TURBO MINIPREP kits (Qiagen), and always had an A260/A280>1.7. Concentrated solutions of DNA were diluted in the gelatin solution so to keep the gelatin concentration >0.017% and, unless otherwise specified, final plasmid DNA concentrations were 0.033 μg/μl. To express GFP the EGFP construct in pBABEpuro was used.

After drying, the DNA spots are briefly exposed to a lipid transfection reagent, the slide is placed in a culture dish and covered with adherent mammalian cells in media. The EFFECTENE™ transfection kit (301425, Qiagen) was used as follows. In a 1.5 ml microcentrifuge tube, 16 μl enhancer was added to 150 μl EC buffer, mixed, and incubated for 5 minutes at room temperature. 25 μl EFFECTENE™ lipid was added, mixed and the entire volume pipetted onto a 40×20 mm cover well (PC200, Grace Bio-Labs). A slide with the printed side down was placed on the cover well such that the solution covers the entire arrayed area while also creating an airtight seal. After a 10 minute incubation⁻, the cover well was pried off the slide with a forceps and the transfection reagent removed carefully by vacuum aspiration. The slide was placed printed side up in a 100×100×10 mm square tissue culture dish and a $1 \times 10^7$ actively growing HEK293T cells in 25 ml media (DMEM with 10% FBS, 50 units/ml penicillin and 50 μg/ml streptomycin) were poured into the dish. Three slides can be transfected side-by-side in this fashion. The cells grew on the slide for 40 hours prior to fixing for 20 minutes at room temperature in 3.7% paraformaldehyde/4.0% sucrose in PBS. Other commonly used mammalian cells lines, such as HeLa and A549 cells, were also tested and similar results were obtained but with transfection efficiencies of 30–50% of those obtained with HEK293 cells. The DNA in the gelatin gel is insoluble in cell culture media but readily enters cells growing on it to create the transfected cell microarray.

To illustrate the method, an array with elements containing an expression construct for the green fluorescent protein (GFP) was printed. HEK293 cells were plated on the slide for transfection and the fluorescence of the cells detected with a laser fluorescence scanner. Microarrays were imaged at a resolution of 5 μm with a laser fluorescence scanner (SCANARRAY™ 5000, GSI Lumonics). GFP and cy3 emission was measured separately after sequential excitation of the two fluorophores. To obtain images at cellular resolution, cells were photographed with a conventional fluorescent microscope. All images were pseudocolored and superimposed using PHOTOSHOP™ 5.5 (Adobe Systems).

A low magnification scan showed a regular pattern of fluorescent spots that matches the pattern in which the GFP expression construct was printed (FIG. 4B). A higher magnification image obtained via fluorescence microscopy showed that each spot is about 150 Fm in diameter and consists of a cluster of 30–80 fluorescent cells (FIG. 4C). As in a conventional transfection, the total expression level in the clusters is proportional over a defined range to the amount of plasmid DNA used (FIG. 4D). Since it may be useful to express two different plasmids in the same cells, whether the technique is compatible with cotransfection was examined. Arrays with elements containing expression constructs for GFP, an epitope-tagged protein or both were prepared and transfected. The cells growing on elements printed with both cDNAs express both encoded proteins, indicating that cotransfection had occurred (FIG. 4E).

Whether transfected cell microarrays could be used to clone gene products based on their intrinsic properties was also determined. As a test case, an array to identify the receptor for FK506, a clinically important immunosuppressant whose pharmacologically relevant target, FKBP12, is an intra-cellular protein, was used (Kino, T., et al., *J. Antiobiot.*, 40:1256 (1987); Harding, M. W., et al., *Nature*, 26:755 (1989)). Elements containing expression constructs for FKBP12, GFP, or both were printed on a slide, in an easily recognizable pattern. After the transfected cell microarray formed, radiolabeled FK506 was added to the tissue culture media for one hour prior to processing the slide for autoradiography and immunofluorescence. The radiolabeled FK506 bound to the array in a pattern of spots that exactly matches the pattern of cell clusters expressing FKBP12 (FIG. 5A). Detection of the bound FK506 with autoradiographic emulsion confirmed, at the cellular level, colocalization between FKBP12 expression and FK506 binding (FIG. 5B). The binding is specific because the GFP-expressing clusters and the non-transfected cells surrounding the clusters showed only background levels of signal (FIG. 5A). Furthermore, the prior addition of excess rapamycin, a competitive antagonist of FK506, completely eliminated the signal. 1 µM rapamycin was added to the cell culture media 30 minutes before the addition of radiolabeled FK506.

The utility of transfected cell microarrays for identifying gene products that induce phenotypes of interest in mammalian cells or have a distinct sub-cellular localization was also explored. Arrays with a collection, enriched for signaling molecules, of 192 distinct epitope-tagged cDNAs in expression vectors were printed. 192 GENESTORM™ expression constructs (Invitrogen) in bacteria were cultured in two 96-well plates and plasmid DNA was purified using the TURBO MINIPREP Kit (Qiagen). Plasmid DNA was diluted with 0.02% gelatin to a final concentration of 0.040 µg/µl and printed. Cellular phosphotyrosine levels were determined by immunofluorescence staining and scanning. Cell morphology and subcellular localization of expressed proteins was assessed by visual inspection via fluorescence microscopy of the cells in the clusters after their detection with anti-V5 immunofluorescence.

After transfection, their effects on cellular phosphotyrosine levels and morphology as well as their subcellular localization were determined. Five cell clusters on grid 1 (A2, C7, C9, C11, and F6) had phosphotyrosine levels above background (FIG. 5C). The coordinates of the clusters match those of the wells of a microtiter plate containing the source cDNAs and were used to look up the identity of the transfected cDNAs. This revealed that four of these clusters were transfected with known tyrosine kinases (trkC, syk, syn, and blk) while the fifth (C11) encodes a protein of unknown function. Simple visual examination of the morphology of the cells in the transfected clusters revealed a diversity of cellular phenotypes even in this small set of clones. In array 2, cluster E8 had fragmented cells characteristic of apoptosis while in two clusters (D10 and F7) the cells were closely attached to each other (FIG. 5D). The presence of apoptotic cells was confirmed by TUNEL (Terminal deoxynucleotidyl transferase mediated dUTP-biotin nick end labeling method) staining. TUNEL staining was performed as described (Y. Gavrieli, Y. Sherman, S. A. Ben-Sasson. *J. Cell Biol.* 119, 493 (1992)).

The observed phenotypes are consistent with the presumed functions of the cDNAs expressed in these clusters (the Table). Subcellular localization of the expressed proteins was examined through visual inspection and those with distinct patterns were noted (the Table). This revealed that several proteins that are known transcription factors were mainly located in the cell nucleus. This was also true for other proteins, such as phosphatase 1-beta, whose subcellular distribution has not been previously ascertained.

TABLE

Description of selected cDNAs expressed in the transfected cell microarray. Shown are the coordinates, the phenotype or property detected, the Genbank accession number and the name of the cDNA. nuc/cyto means nuclear and cytoplasmic staining was visible.

| Grid: Coordinate | Phenotype/property | Accession number | Function |
|---|---|---|---|
| 2:E8 | apoptosis | AF016266 | TRAIL receptor 2 |
| 2:D10 | cell adhesion | X97229 | NK receptor |
| 2:F7 | cell adhesion | M98399 | CD36 |
| 1:A9 | nuclear | U11791 | Cyclin H |
| 1:B5 | nuclear | M60527 | deoxycytidine kinase |
| 1:B12 | nuclear | M60724 | p70 S6 kinase kinase α1 |
| 1:C12 | nuclear | M90813 | D-type cyclin |
| 1:E4 | mitochondrial | U54645 | methylmalonyl-coA mutase |
| 1:E10 | mitochondrial | J05401 | creatine kinase |
| 1:G9 | nuc/cyto | U40989 | tat interactive protein |
| 1:G10 | nuc/cyto | U09578 | MAPKAP (3pk) kinase |
| 2:A9 | nuclear | X83928 | TFIID subunit TAFII28 |
| 2:A12 | nuc/cyto | M62831 | ETR101 |
| 2:B6 | nuc/cyto | X06948 | IgE receptor α-subunit |
| 2:B12 | nuclear | X63469 | TFIIE β subunit |
| 2:C5 | nuclear | M76766 | General transcription factor IIB |
| 2:C7 | nuc/cyto | M15059 | CD23A |
| 2:C12 | nuclear | X80910 | PP1, β catalytic subunit |
| 2:D4 | nuclear | AF017307 | Ets-related transcription factor |
| 2:E7 | nuclear | X63468 | TFIIE α |
| 2:E12 | nuclear | U22662 | Orphan receptor LXR-α |
| 2:F8 | nuclear | L08895 | MEF2C |

TABLE-continued

Description of selected cDNAs expressed in the transfected cell microarray. Shown are the coordinates, the phenotype or property detected, the Genbank accession number and the name of the cDNA. nuc/cyto means nuclear and cytoplasmic staining was visible.

| Grid: Coordinate | Phenotype/property | Accession number | Function |
| --- | --- | --- | --- |
| 2:F12 | nuclear | AF028008 | SP1-like transcription factor |
| 2:G2 | nuc/cyto | U37352 | PP2A, regulatory B' α 1 subunit |
| 2:G3 | nuc/cyto | L14778 | PP2B, catalytic α subunit |

The microarrays can be printed with the same robotic arrayers as traditional DNA arrays, so it is feasible to achieve densities of up 10,000–15,000 cell clusters per standard slide. At these densities the entire set of human genes can be expressed on a small number of slides, allowing rapid pan-genomic screens. Thus, comprehensive collections of full-length cDNAs for all mammalian genes can be generated (Strausberg, R. L., et al., *Science,* 15:455 (1999)) and will be valuable tools for making such arrays.

Transfected cell microarrays have distinct advantages over conventional expression cloning strategies using FACs or sib selection (Simonsen, H., et al., *Trends Pharmacol. Sci.* 15:437 (1994)). First, cDNAs do not need to be isolated from the cells exhibiting the phenotype of interest. This allows for screens using a variety of detection methods, such as autoradiography or in situ hybridization, and significantly accelerates the pace of expression cloning. The experiments described herein took days to perform instead of the weeks to months necessary with other expression cloning strategies. Second, transfected cell microarrays can also be used to screen living cells, allowing the detection of transient phenotypes, such as changes in intracellular calcium concentrations. Third, being compact and easy to handle, transfected cell microarrays have economies of scale. The arrays are stable for months and can be printed in large numbers, allowing many phenotypes to be screened in parallel, with a variety of methods, in a small number of tissue culture plates.

Described herein are arrays in which the transfected plasmids direct gene overexpression. However, as antisense technology improves or other methods emerge for decreasing gene function in mammalian cells, it is likely that transfected cell microarrays can be used to screen for phenotypes caused by loss of gene function. Lastly, the immobilization of the plasmid DNA in a degradable gel is the key to spatially restricting transfection without wells.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of introducing nucleic acid molecules into eukaryotic cells, said method comprising the steps of:
   (a) depositing a nucleic acid molecule-containing mixture onto a surface, wherein said nucleic acid molecule-containing mixture comprises (i) nucleic acid molecules to be introduced into eukaryotic cells and (ii) a gelatin;
   (b) affixing said nucleic acid molecule-containing mixture to said surface; and
   (c) plating eukaryotic cells onto said surface at a density of $0.3 \times 10^5 / cm^2$ to $3.0 \times 10^5 / cm^2$ under appropriate conditions for entry of said nucleic acid molecules into said cells.

2. The method of claim 1, further comprising the steps after step (b) of:
   (i) covering said surface bearing said nucleic acid molecule-containing mixture with an appropnate amount of a transfection reagent and maintaining the resulting product under conditions appropriate for complex formation between said nucleic acid molecules and said transfection reagent; and
   (ii) removing the non-complexed transfection reagent.

3. The method of claim 1, wherein said nucleic acid molecule-containing mixture further comprises a sugar, a buffer that facilitates nucleic acid molecule condensation, and a transfection reagent.

4. The method of claim 1, wherein each nucleic acid molecule to be introduced is contained in a vector.

5. The method of claim 4, wherein said vector is a plasmid or a viral-based vector.

6. The method of claim 1, wherein said nucleic acid molecules are expressed in said cells.

7. The method of claim 1, wherein said cells are plated at a density of $0.5 \times 10^5 / cm^2$ to $2.0 \times 10^5 / cm^2$.

8. The method of claim 1, wherein said nucleic acid molecules are DNA or RNA molecules.

9. The method of claim 8, wherein said nucleic acid molecules are DNA molecules.

10. The method of claim 9, wherein the concentration of said DNA molecules is 0.01 $\mu g/\mu l$ to 0.5 $\mu g/\mu l$.

11. A method of introducing nucleic acid molecules into eukaryotic cells, said method comprising the steps of:
    (a) depositing a nucleic acid molecule-containing mixture onto a surface, wherein the nucleic acid molecule-containing mixture comprises (i) nucleic acid molecules to be introduced into eukaryotic cells and (ii) a gelatin, wherein the concentration of nucleic acid molecules in said nucleic acid molecule-containing mixture is 0.01 $\mu g/\mu L$ to 0.5 $\mu g/\mu L$;
    (b) affixing said nucleic acid molecule-containing mixture to said surface; and
    (c) plating eukaryotic cells onto said surface in sufficient density and under appropriate conditions for entry of said nucleic acid molecules into said cells.

12. The method of claim 11, further comprising the steps after step (b) of:
    (i) covering said surface bearing said nucleic acid molecule-containing mixture with an appropriate amount of a transfection reagent and maintaining the resulting product under conditions appropriate for complex formation between said nucleic acid molecules and said transfection reagent; and
    (ii) removing the non-complexed transfection reagent.

13. The method of claim 11, wherein said nucleic acid molecule-containing mixture further comprises a sugar, a buffer that facilitates nucleic acid molecule condensation, and a transfection reagent.

14. The method of claim 11, wherein each nucleic acid molecule to be introduced is contained in a vector.

15. The method of claim 14, wherein said vector is a plasmid or a viral-based vector.

16. The method of claim 11, wherein said eukaryotic cells are mammalian cells.

17. The method of claim 11, wherein said gelatin is present in said nucleic acid molecule-containing mixture at a concentration ranging from about 0.05% to about 0.5%.

18. A method of introducing nucleic acid molecules into eukaryotic cells, said method comprising the steps of:
    (a) depositing a nucleic acid molecule-containing mixture onto a surface, wherein the nucleic acid molecule-containing mixture comprises (i) nucleic acid molecules to be introduced into eukaryotic cells and (ii) a gelatin, wherein said gelatin is present at a concentration from about 0.05% to about 0.5%;
    (b) affixing said nucleic acid molecule-containing mixture to said surface; and
    (c) plating eukaryotic cells onto said surface in sufficient density and under appropriate conditions for entry of said nucleic acid molecules into said eukaryotic cells.

19. The method of claim 18, further comprising the steps after step (b) of:
    (i) covering said surface bearing said nucleic acid molecule-containing mixture with an appropriate amount of a transfection reagent and maintaining the resulting product under conditions appropriate for complex formation between said nucleic acid molecules and said transfection reagent; and
    (ii) removing the non-complexed transfection reagent.

20. The method of claim 18, wherein said nucleic acid molecule-containing mixture further comprise a sugar, a buffer that facilitates nucleic acid molecule condensation, and a transfection reagent.

21. The method of claim 18, wherein each nucleic acid molecule to be introduced is contained in a vector.

22. The method of claim 21, wherein said vector is a plasmid or a viral-based vector.

23. The method of claim 18, wherein said eukaryotic cells are mammalian cells.

24. The method of claim 18, wherein said nucleic acid molecules are DNA or RNA molecules.

25. The method of claim 24, wherein said nucleic acid molecules are DNA molecules.

26. The method of claim 18, wherein the concentration of gelatin is from about 0.1% to about 0.2%.

27. A method of introducing nucleic acid molecules into eukaryotic cells, said method comprising the steps of:
(a) depositing a nucleic acid molecule-containing mixture onto a surface, wherein said nucleic acid molecule-containing mixture comprises:
  (i) nucleic acid molecules to be introduced into eukaryotic cells,
  (ii) a gelatin, wherein said gelatin is present at a concentration from about 0.01% to about 0.05%.
  (iii) a sugar,
  (iv) a buffer that facilitates nucleic acid molecule condensation, and
  (v) a transfection reagent;
(b) affixing said nucleic acid molecule-containing mixture to said surface; and
(c) plating eukaryotic cells onto said surface in sufficient density and under appropriate conditions for entry of said nucleic acid molecules in said nucleic acid molecule-containing mixture into said eukaryotic cells.

28. The method of claim 27, further comprising the steps after step (b) of:
(i) covering said surface bearing said nucleic acid molecule-containing mixtures with an appropriate amount of a transfection reagent and maintaining the resulting product under conditions appropriate for complex formation between said nucleic acid molecules in said nucleic acid molecule-containing mixture and said transfection reagent; and
(ii) removing the non-complexed transfection reagent.

29. The method of claim 27, wherein each nucleic acid molecule to be introduced is contained in a vector.

30. The method of claim 29, wherein said vector is a plasmid or a viral-based vector.

31. The method of claim 30, wherein said eukaryotic cells are mammalian cells.

32. The method of claim 27, wherein said cells are plated at a density of $0.3 \times 10^5/cm^2$ to $3.0 \times 10^5/cm^2$.

33. The method of claim 27, wherein said nucleic acid molecules DNA or RNA molecules.

34. The method of claim 33, wherein said nucleic acid molecules are DNA molecules.

35. The method of claim 34, wherein the concentration of said DNA molecules is 0.01 $\mu g/\mu l$ to 0.5 $\mu g/\mu l$.

36. The method of claim 27, wherein said sugar is sucrose ranging in concentration from about 0.1M to about 0.4M.

* * * * *

UNITED STATES PATENT AND TRADEMARK OFFICE
CERTIFICATE OF CORRECTION

PATENT NO.       : 6,951,757 B2
APPLICATION NO. : 10/379130
DATED            : October 4, 2005
INVENTOR(S)      : Sabatini It is certified that error appears in the above-identified patent and that said Letters Patent is hereby corrected as shown below:

Column 3, Line 54, replace "Σpoly-L-lysine" with --Σ poly-L- lysine--.

Column 11, Line 14ff., replace "intrac-ellular" with --intra-cellular--.

Column 12, Line 36, replace "a episomal" with --an episomal--.

Column 14,
Line 1, replace "can include be" with --can be--;
Line 12ff., replace "Chomc-zynski" with --Chom-czynski--;
Line 15ff., replace "stre-pavidin" with --strept-avidin --; and
Line 29, replace "eukaryoties" with --eukaryotes--.

Column 16,
Line 25, replace "initial is SGE" with --initial SGE--; and
Line 47, replace "84:4171), " with --84:4171,--.

Column 22,
Line 46, replace "nitrocelluloes" with --nitrocellulose--; and
Line 48ff., replace "nitrocellulosemem-brane" with --nitrocellulose mem-brane--.

Column 23, Line 59, replace "*Ustilaqo*" with --*Ustilago*--.

UNITED STATES PATENT AND TRADEMARK OFFICE
CERTIFICATE OF CORRECTION

PATENT NO. : 6,951,757 B2
APPLICATION NO. : 10/379130
DATED : October 4, 2005
INVENTOR(S) : Sabatini It is certified that error appears in the above-identified patent and that said Letters Patent is hereby corrected as shown below:

Column 26,
Line 49, replace "abti-phosphosthreonine" with --anti-phosphothreonine--; and
Line 59, replace "lose" with --loss--.

Column 27,
Line 10, replace "102." with --102).--; and
Line 38ff., replace "chromogenic/fluorscent" with --chromogenic/fluorescent--.

Column 33, Line 32, replace "ortoxicology other tests" with --or other toxicology tests--.

Column 34, Line 64, replace "QIAPREP" with --QIAPREP$^{TM}$--.

Column 35, Line 13, replace "eppendorf" with --Eppendorf--.

Column 36, Line 65, replace "EFFECTENE" with --EFFECTENE$^{TM}$--.

Column 43, Line 28, Claim 2, replace "appropnate" with --appropriate--.

Signed and Sealed this

Twenty-second Day of August, 2006

JON W. DUDAS
*Director of the United States Patent and Trademark Office*

SEQUENCE LISTING

<160> NUMBER OF SEQ ID NOS: 3

<210> SEQ ID NO 1
<211> LENGTH: 14
<212> TYPE: DNA
<213> ORGANISM: Artificial Sequence
<220> FEATURE:
<223> OTHER INFORMATION: Synthetic

<400> SEQUENCE: 1
gcttggatcc aagc                                                      14

<210> SEQ ID NO 2
<211> LENGTH: 6
<212> TYPE: DNA
<213> ORGANISM: Artificial Sequence
<220> FEATURE:
<223> OTHER INFORMATION: Synthetic

<400> SEQUENCE: 2 ggatcc                                                                6

<210> SEQ ID NO 3
<211> LENGTH: 6
<212> TYPE: DNA
<213> ORGANISM: Artificial Sequence
<220> FEATURE:

-continued

<223> OTHER INFORMATION: Synthetic

<400> SEQUENCE: 3 aagctt                                                                  6